(12) United States Patent
French et al.

(10) Patent No.: US 6,290,949 B1
(45) Date of Patent: *Sep. 18, 2001

(54) ADENOVIRAL VECTOR FOR INHIBITING RESTENOSIS

(76) Inventors: Brent A. French, 5746 Cheena Dr., Houston, TX (US) 77096; Albert E. Raizner, 11945 N. Durrette, Houston, TX (US) 77024; Robert Roberts, 2198 Troon Rd., Houston, TX (US) 77019

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/653,824

(22) Filed: May 28, 1996

Related U.S. Application Data

(63) Continuation of application No. 08/114,222, filed on Sep. 1, 1993, now abandoned, which is a continuation-in-part of application No. 08/063,751, filed on May 20, 1993, now abandoned.

(51) Int. Cl.$^7$ .......................... A61K 48/00; A01N 63/00; C12N 15/00
(52) U.S. Cl. .......................... 424/93.2; 424/93.6; 514/44; 435/320.1; 435/456
(58) Field of Search .......................... 514/44; 435/172.3, 435/172.1, 320.1, 455, 456; 536/23.1, 23.2, 23.4, 23.5; 935/52, 55; 424/93.2, 93.6

(56) References Cited

U.S. PATENT DOCUMENTS 5,328,470 * 7/1994 Nabel et al. .......................... 604/101

OTHER PUBLICATIONS

Rosenfeld et al (Jan. 10, 1992) Cell 68: 143–155.*
Uhlmann et al (Jun. 1990) Chemical Reviews 90: 544–584.*
Karson et al (Jun. 1992) J. Reproductive Med. 37: 508–514.*
Ledley (1991) Human Gene Therapy 2: 77–83.*
Nabel et al (Sep. 14, 1990) Science 249:285–1288.*
Forrester et al (Mar. 1, 1991) J. Am. College of Cardiol. 17: 758–769.*
Brauner R. Wu L. Laks H. Nonoyama M. Scholl F. Shvarts O. Berk A. Drinkwater DC Jr. Wang JL. Intracoronary gene transfer of immunosuppressive cytokines to cardiac allografts: method and efficacy of adenovirus–mediated transduction. Journal of Thoracic & Cardiovascular Surgery. 113(6):1059–66, Jun. 1997.
Burcin MM. Schiedner G. Kochanek S. Tsai SY. O'Malley BW. Adenovirus–mediated regulable target gene expression in vivo. Proceedings of the National Academy of Sciences of the United States of America. 96(2):355–60, Jan. 19. 1999.

Chen L. Chen D. Block E. O'Donnell M. Kufe DW. Clinton SK. Eradication of murine bladder carcinoma by intratumor injection of a bicistronic adenoviral vector carrying cDNAs for the IL–12 heterodimer and its inhibition by the IL–12 p40 subunit homodimer. Journal of Immunology. 159(1):351–9, Jul. 1, 1997.

DeYoung MB. Zamarron C. Lin AP. Qiu C. Driscoll RM. Dichek DA. Optimizing vascular gene transfer of plasminogen activator inhibitor 1. Human Gene Therapy. 10(9):1469–78, Jun. 10, 1999.

Faggin E. Puato M. Zardo L. Franch R. Millino C. Sarinella F. Pauletto P. Sartore S. Chiavegato A. Smooth muscle–specific SM22 protein is expressed in the adventitial cells of balloon–injured rabbit carotid artery. Arteriosclerosis, Thrombosis & Vascular Biology. 19(6):1393–404, Jun. 1999.

Franz WM. Rothmann T. Frey N. Katus HA. Analysis of tissue–specific gene delivery by recombinant adenoviruses containing cardiac–specific promoters. Cardiovascular Research. 35(3):560–6, Sep. 1997.

Henke PK. DeBrunye LA. Strieter RM. Bromberg JS. Prince M. Kadell AM. Sarkar M. Londy F. Wakefield TW. Viral IL–10 gene transfer decreases inflammation and cell adhesion molecule expression in a rat model of venous thrombosis. Journal of Immunology, 164(4):2131–41, Feb. 15, 2000.

Jeng MH. Kao C. Sivararnan L. Krnacik S. Chung LW. Medina D. Conneely OM. O'Malley BW. Reconstitution of estrogen–dependent transcriptional activation of an adenoviral target gene in select regions of the rat mammary gland. Endocrinology. 139(6);2916–25, Jun. 1998.

Kim S. Lin H. Barr E. Chu L. Leiden JM. Parmacek MS. Transcriptional targeting of replication–defective adenovirus transgene expression to smooth muscle cells in vivo. Journal of Clinical Investigation. 100(5):1006–14, Sep. 1, 1997.

(List continued on next page.)

*Primary Examiner*—Deborah Crouch
(74) *Attorney, Agent, or Firm*—Peter J. Davis

(57) ABSTRACT

Gene transfer vectors, especially adenoviral vectors, and synthetic vectors capable of emulating specific viral functions, that carry gene sequences capable of ameliorating or preventing the symptoms of cardiovascular disease are disclosed. Such methods can be used to treat restenosis, especially when incident to injury by angioplasty.

7 Claims, 5 Drawing Sheets

OTHER PUBLICATIONS

Kim KS. Takeda K. Sethi R. Pracyk JB. Tanaka K. Zhou YF. Yu ZX. Ferrans VJ. Bruder JT. Kovesdi I. Irani K. Goldschmidt–Clermont P. Finkel T. Protection from reoxygenation injury by inhibition of rac1. Journal of Clinical Investigation. 101(9):1821–6, May 1, 1998.

Laukkanen J. Lehtolainen P. Gough PJ. Greaves DR. Gordon S. Yla–Herttuala S. Adenovirus–mediated gene transfer of a secreted form of human macrophage scavenger receptor inhibits modified low–density lipoprotein degradation and foam–cell formation in macrophages. Circulation. 101(10):1091–6, Mar. 14, 2000.

Li J. Fang B. Eisensmith RC. Li XH. Nasonkin I. Lin–Lee YC. Mims MP. Hughes A. Montgomery CD. Roberts JD. et al. In vivo gene therapy for hyperlipidemia: phenotypic correction in Watanabe rabbits by hepatic delivery of the rabbit LDL receptor gene. Journal of Clinical Investigation. 95(2): 768–73, Feb. 1995.

Li Q. Bolli R. Qiu Y. Tang XL. Murphree SS. French BA. Gene therapy with extracellular superoxide dismutase attenuates myocardial stunning in conscious rabbits. Circulation. 98(14):1438–48, Oct. 6, 1998.

Lin P. Buxton JA. Acheson A. Radziejewski C. Maisonpierre PC. Yancopoulos GD. Channon KM. Hale LP. Dewhirst MW. George SE. Peters KG. Antiangiogenic gene therapy targeting the endothelium–specific receptor tyrosine kinase Tie2. Proceedings of the National Academy of Sciences of the United States of America. 95(15):8829–34, Jul. 21, 1998.

Lund DD. Faraci FM. Miller FJ Jr. Heistad DD. Gene transfer of endothelial nitric oxide synthase improves relaxation of carotid arteries from diabetic rabbits. Circulation. 101(9):1027–33, Mar. 7, 2000.

Macejak DG. Lin H. Webb S. Chase J. Jensen K. Jarvis TC. Leiden JM. Couture L. Adenovirus–mediated expression of a ribozyme to c–myb mRNA inhibits smooth muscle cell proliferation and neointima formation in vivo. Jornal of Virology. 73(9):7745–51, Sep. 1999.

Murry CE. Kay MA. Bartosek T. Hauschka SD. Schwartz SM. Muscle differentiation during repair of myocardial necrosis in rats via gene transfer with MyoD. Journal of Clinical Investigation. 98(10):2209–17, Nov. 15, 1996.

Neschis DG. Safford SD. Hanna AK. Fox JC. Golden MA. Antisense basic fibroblast growth factor gene transfer reduces early intimal thickening in a rabbit femoral artery balloon injury model. Journal of Vascular Surgery. 27(1):126–34, Jan. 1998.

Ohno T. Gordon D. San H. Pompili VJ. Imperiale MJ. Nable GJ. Nabel EG. Gene therapy for vascular smooth muscle cell proliferation after arterial injury. Science. 265(5173):781–4, Aug. 5, 1994.

Qi Z. Atsuchi N. Ooshima A. Takeshita A. Ueno H. Blockade of type beta transforming growth factor signaling prevents liver fibrosis and dysfunction in the rat. Proceedings of the National Academy of Sciences of the United States of America. 96(5):2345–9, Mar. 2, 1999.

Rade JJ. Schulick AH. Virmani R. Dichek DA. Local adenoviral–mediated expression of recombinant hirudin reduces neointima formation after arterial injury. Nature Medicine. 2(3):293–8, Mar. 1996.

Rosengart TK. Lee LY. Patel SR. Sanborn TA. Parikh M. Bergman GW. Hachamovitch R. Szulc M. Kligfield PD. Okin PM. Hahn RT. Devereux RB. Post MR. Hackett NR. Foster T. Grasso TM. Lesser ML. Isom OW. Crystal RG. Angiogenesis gene therapy: phase I assessment of direct intramyocardial administration of an adenovirus vector expressing VEGF121 cDNA to individuals with clinically significant severe coronary artery disease. Circulation. 100(5):468–74, Aug. 3, 1999.

Scheinman M. Ascher E. Levi GS. Hingorani A. Shirazian D. Seth P. p53 gene transfer to the injured rat carotid artery decreases neointimal formation. Journal of Vascular Surgery. 29(2):360–9, Feb. 1999.

Smith JD. Bryant SR. Couper LL. Vary CP. Gotwals PJ. Koteliansky VE. Lindner V. Soluble transforming growth factor–beta type II receptor inhibits negative remodeling, fibroblast transdifferentiation, and intimal lesion formation but not endothelial growth. Circulation Research 84(10):1212–22, May 28, 1999.

Tangirala RK. Tsukamoto K. Chun SH. Usher D. Pure E. Rader DJ. Regression of atherosclerosis induced by liver–directed gene transfer of apolipoprotein A–1 in mice. Circulation. 100(17):1816–22, Oct. 26, 1999.

Varenne O. Pislaru S. Gillijns H. Van Pelt N. Gerard RD. Zoldhelyi P. Van de Werf F. Collen D. Janssens SP. Local adenovirus–mediated transfer of human endothelial nitric oxide synthase reduces luminal narrowing after coronary angioplasty in pigs. Circulation. 98(9):919–26, Sep. 1, 1998.

Weber KS. Draude G. Erl W. de Martin R. Weber C. Monocyte arrest and transmigration on inflamed endothelium in shear flow is inhibited by adenovirus–mediated gene transfer of IkappaB–alpha. Blood. 93(11):3685–93, Jun. 1, 1999.

White DC. Hata JA. Shah AS. Glower DD. Lefkowitz RJ. Koch WJ. Preservation of myocardial beta–adrenergic receptor signaling delays the development of heart failure after myocardial infarction. Proceedings of the National Academy of Sciences of the United States of America. 97(10):5428–33, May 9, 2000.

Woo YJ. Zhang JC. Vijayasarathy C. Zwacka RM. Englehardt JF. Gardner TJ. Sweeney HL. Recombinant adenovirus–mediated cardiac gene transfer of superoxide dismutase and catalase attenuates postischemic contractile dysfunction. Circulaton. 98(19 Suppl):II255–60, Nov. 10, 1998.

Yang GY. Mao Y. Zhou LF. Ye W. Liu XH. Gong C. Lorris Betz A. Attenuation of temporary focal cerebral ischemic inj.

Nabel et al. (1990) Science 249, 1285–1288.*

Forrester et al. (1991) J. Am. Coll. Cardol. 17, 758–769.*

Rosenfeld et al. (1992) Cell 68, 143–155.*

Blau et al (Nov. 2, 1995) New Eng. J. Med., 1204–1207.*

Science vol. 269, pp. 1050–1055.*

* cited by examiner

ADENOVIRAL VECTOR FOR INHIBITING RESTENOSIS

CROSS-REFERENCE TO RELATED APPLICATIONS

This application is a continuation-in-part of 08/114222 filed Sep. 1, 1993 Abn., which is a CIP of 08/063,751 filed May 20, 1993 Abn.

FIELD OF THE INVENTION

The invention relates to therapeutic agents for the prevention and treatment of cardiovascular disease. More specifically, the invention relates to modified viruses and/or synthetic complexes capable of emulating specific viral functions. It further relates to the use of such modified viruses in a genetic therapy for cardiovascular disease.

BACKGROUND OF THE INVENTION

I. Restanosis and Cardiovascular Disease

Stenosis denotes a narrowing or constriction of a duct or canal. A variety of disease processes, such as atherosclerotic lesions, immunological reactions, congenital deformities, etc., can lead to the stenosis of coronary arteries and thus to myocardial ischemia. Percutaneous transluninal coronary angioplasty (PTCA), the insertion and partial inflation of a balloon catheter into a stenotic vessel to effect its repair, has been extensively used to treat stenosis. In 1990, over 300,000 procedures were performed in the United States alone.

The major limitation of PTCA is restenosis (i.e. the re-constriction) of the vascular lesion (Liu, M. W. et al., Circulation 79:1374–1386 (1989), herein incorporated by reference). Restenosis has been found to occur in 30% to 40% of angioplasty patients within 6 months of the procedure (Califf, R. M. et al., J. Amer Col. Cardiol. 172B-13B (1991), McBride, W. et al., N. Engl. J. Med. 31:1734–1737 (1988)). Restenosis develops so rapidly that it may be considered a form of accelerated atherosclerosis induced by injury. The significance of the high restenosis, rate is compounded by the present inability to predict with a high degree of certainty which patients, vessels, or lesions will undergo restenosis. Indeed, arteries that are widely patent 2 days after PTCA, free of obstructive thrombus, have exhibited restenosis at catheterization 4–6 months later (Liu, M. W. et al., Circulation 79:1374–1386 (1989)).

The mechanism of restenosis is thus not fully understood. The angioplasty procedure causes unavoidable injury to arterial walls. Animal studies of atherosclerosis have suggested that after such balloon injury, denudation of endothelial cells occurs, followed by platelet adhesion and aggregation, and by the release of platelet-derived growth factor (PDGF) as well as other growth factors. The basic biologic factors believed to be involved in the occurrence of restenosis include: the extent of injury, platelets, inflammatory cells, growth factors, cytokines, endothelial cells, smooth muscle cells, and extracellular matrix production.

Both early platelet aggregation and thrombus formation, as well as late myointimal proliferation, are believed to affect the development of the recurrent lesions after PTCA (Liu, M. W. et al., Circulation 79:1374–1386 (1989)). Although such platelet-thrombus accumulation appears to be a contributing factor in restenosis after balloon dilatation, direct and indirect evidence strongly supports the concept of intimal hyperplasia or proliferation, and migration of vascular smooth muscle cells (VSNC) of medial, or possibly of intimal, origin as the fundamental process of restenosis (see, for review, Liu, M. W. et al., Circulation 79:1374–1386 (1989)). In particular, atherosclerotic coronaries injured by oversized angioplasty balloons, and atherosclerotic coronaries injured by the deployment of intracoronary stents have been found to display vigorous VSMC migration and proliferation (Rodgers, G. P. et al., Circulation 82:560 (1990); Schwartz, R. S. et al., Circulation 82:2190 (1990); Karas, S. P. et al, J. Amer. Col. Cardiol. 20:467 (1992); Johnson, D. E. et al, Circulation 78(suppl.) II1:II-82 (1988), all herein incorporated by reference). There is also a large body of indirect and experimental data. Intimal thickening induced by balloon injury in normal rat arteries reaches its maximum at 2 months, a time course of the intimal growth that approximates that observed in humans after PTCA (Serruys, P. W. et al., Circulation 77:361–371 (1988)). Intimal hyperplasia is also known to be an important component of restenosis in the atherosclerotic rabbit artery. Medial smooth muscle cells are the major cellular component of the arterial wall, and the intimal proliferation of those cells is the only major reparative or reactive response of the arterial wall to mechanical or inflammatory injury.

In their normal quiescent state, smooth muscle cells proliferate at a very low rate (probably less than 0.1% per day), in response to the presence of growth inhibitory factors, such as heparin. In contrast, endothelial cells, macrophages, and platelets are thought to provide the mitogenic stimulus necessary to the growth of medial smooth muscle cells in normal vessels (Liu, N. W. et al., Circulation 79:1374–1386 (1989)). It has been proposed that situations such as vessel damage cause platelets to aggregate on the angioplasty-induced wound surface. These activated platelets release substances that promote local vasoconstriction and thrombus formation and growth factors that activate mesenchymal cells in the vicinity of injured tissue. Within a few hours sonocytes also appear, increasing in number over the first few days. Like platelets, monocytes secrete growth factors capable of initiating and promoting local tissue mesenchymal cell migration. Such activated platelets and cells produce and release a number of growth stimulating factors (such as platelet derived growth factor (PDGF), epidermal growth factors, insulin-like growth factors, transforming growth factors (TGF-$\alpha$ and TGF-$\beta$), PDGF-like molecules, fibroblast growth factors (acidic and basic), interleukin-1 and somatomedin-C, etc.) that are capable of inducing muscle cell proliferation (Liu, M. W. et al., Circulation 79:1374–1386 (1989); Forrester, J. S. et al., J. Amer. Col. Cardiol. 17:758–769 (1991); Stiles, C. D. et al., J. Supramolec. Struct. 11:489–499 (1980)). In this manner, PDGF and other growth factors are released from platelets and other cells to assist in the repair process.

Studies examining the proliferative activity of smooth muscle cells have found that most enter the growth cycle between 2 and 3 days after balloon injury and the vast majority of proliferation is completed within 7 days Clowes, A. W. et al., Circ. Res. 56:139–145 (1985)). In addition, the population of nondividing smooth muscle cells remains relatively constant between 7 and 14 days, suggesting that if smooth muscle cells proliferate, they do so soon after injury. Smooth muscle cell proliferation thus appears to be an acute response related to the initial injury.

II. Treatient of Restenosis

Mechanical approaches aimed at minimizing or preventing restenosis with atherectomy devices, stents, or specialized balloon catheters have not, to date, significantly reduced the restenosis rate (Waller, B. F., J Amer. Col.

Cardiol. 21:969–987 (1989)). Systemic drug therapy has yet to be effective (Chesebro, J. H. et al., *Circulation* 80:II-64 (1989); Pepine, C. J. et al., *Circulation* 81:1753–1761 (1990); Liu, N. W. et al., *Circulation* 79:1374–1386 (1989), all herein incorporated by reference)).

Intracoronary site specific gene transfer has been proposed as a means for allowing the production of therapeutic proteins in concentrations sufficient to combat restenosis (Swain, J. L., *Circulation* 80:1495–1496 (1989); O'Brien, T. X. et al., *Circulation* 11:2133–2136 (1991)). The general principles of gene therapy have been discussed by Oldham, R. K. (In: *Principles of Biotherapy*, Raven Press, NY, 1987); Boggs, S. S. (*Int. J. Cell Clon.* 8:80–96 (1990)); Karson, E. M. (*Biol. Reprod.* 42:39–49 (1990)); Ledley, F. D., In: *Biotechnology A Conprehensive Treatise. volume 7B. Gene Technology*, VCH Publishers, Inc. NY, pp 399–458 (1989)); all of which references are incorporated herein by reference.

Despite the potential for intracoronary site specific gene transfer to allow production of therapeutic proteins in concentrations sufficient to combat restenosis, methods involving retroviruses and other transfection approaches have proven to be unsuccessful. Wilson, J. M. et al. (*Science* 24:1344–1346 (1989)) and Nabel, E. G. et al. (*Science* 24:1342–1343 (1989)) have discussed the use of retroviruses to introduce reporter genes into endothelial cells in vitro. The genetically altered cells were reintroduced into vascular segments of intact animals and found to be able to express the marker protein ($\beta$-galactosidase) for at least 5 weeks. In an in vitro study, Dichek, D. A. et al. (*Circulation* 8:1347–1353 (1989) discussed the ability of cDNA-transfected sheep endothelial cells that had been seeded onto metallic stents to produce physiologically active tissue plasminogen activator.

Nabel, E. G. et al. (*Science* 24:1285–1288 (1990)) discuss the use of a dual-balloon catheter system to directly transfect pig iliofemoral arteries and bypass the steps of in vitro transfection and reimplantation of endothelial cells. Both retroviruses and cationic liposomes were used as vectors. In order to obtain transfection, these investigators incubated femoral artery segments for 30 minutes with DNA-Lipofectin complexes delivered by moans of a dual-balloon catheter that did not provide for perfusion to the distal vasculature. This method proved effective in peripheral vessels, but perfusion of blood to the distal artery would be necessary during coronary transfection in order to avoid cardiac ischemia, arrhythmia or infarction (Chapman, G. D. et al., *Circ. Res.* 71:27–33 (1992)).

As indicated, attempts have been made to use cationic liposomes as the transfection vehicle (Nabel, E. G. et al., *Science* 249:1285–1288 (1990); Lim, C. S. et al., *Circulation* 83:2007–2011 (1991)). Lin, C. S. et al. (*Circulation* 83:2007–2011 (1991)) discuss the direct transfection An vivo of the coronary arteries of an intact canine by a surgical method using cationic liposomes. A recent report by Chapman, G. D. et al. (*Circ. Res.* 21:27–33 (1992)), discusses the possibility of using Lipofectin™-mediated transfection of coronary arteries. As indicated in that report, transfection was extremely inefficient.

Although various researchers have reported in vitro methods for gene transfer, extrapolating from such in vitro work to in vivo intracoronary gene transfer with a catheter technique poses special problems. A prolonged incubation of the gene of interest in the coronary artery is desirable, since in vitro expression of protein is directly, correlated with the duration of exposure of cells to DNA (Chapman, G. D. et al., *Circ. Res.* 71:27–33 (1992); Lim, C. S. et al., *Circulation* 83:2007–2011 (1991)).

Thus, whereas direct in vivo gene transfer into peripheral arteries has been demonstrated using Lipofectin™ or retroviral vectors (Nabel, E. G. et al., *Science* 249:1285–1288 (1990)), and canine coronary arteries have been targeted with Lipofectin™ (Lin, C. S. et al., *Circulation* 83:2007–2011 (1991); Chapman, G. D. et al., *Circ. Res.* 71:27–33 (1992)), the low efficiencies inherent in these gene transfer methods have precluded clinical application.

Thus, the application of gene therapy has been limited by the low efficiencies of gone transfer afforded by conventional and recent methods. In particular, a more efficient technique of gene transfer that would be applicable not only to normal coronary arteries, but also to atherosclerotic vessels, and particularly those displaying the histopathology of restenosis would be highly desirable. The present invention provides such a therapy.

Figure 1:
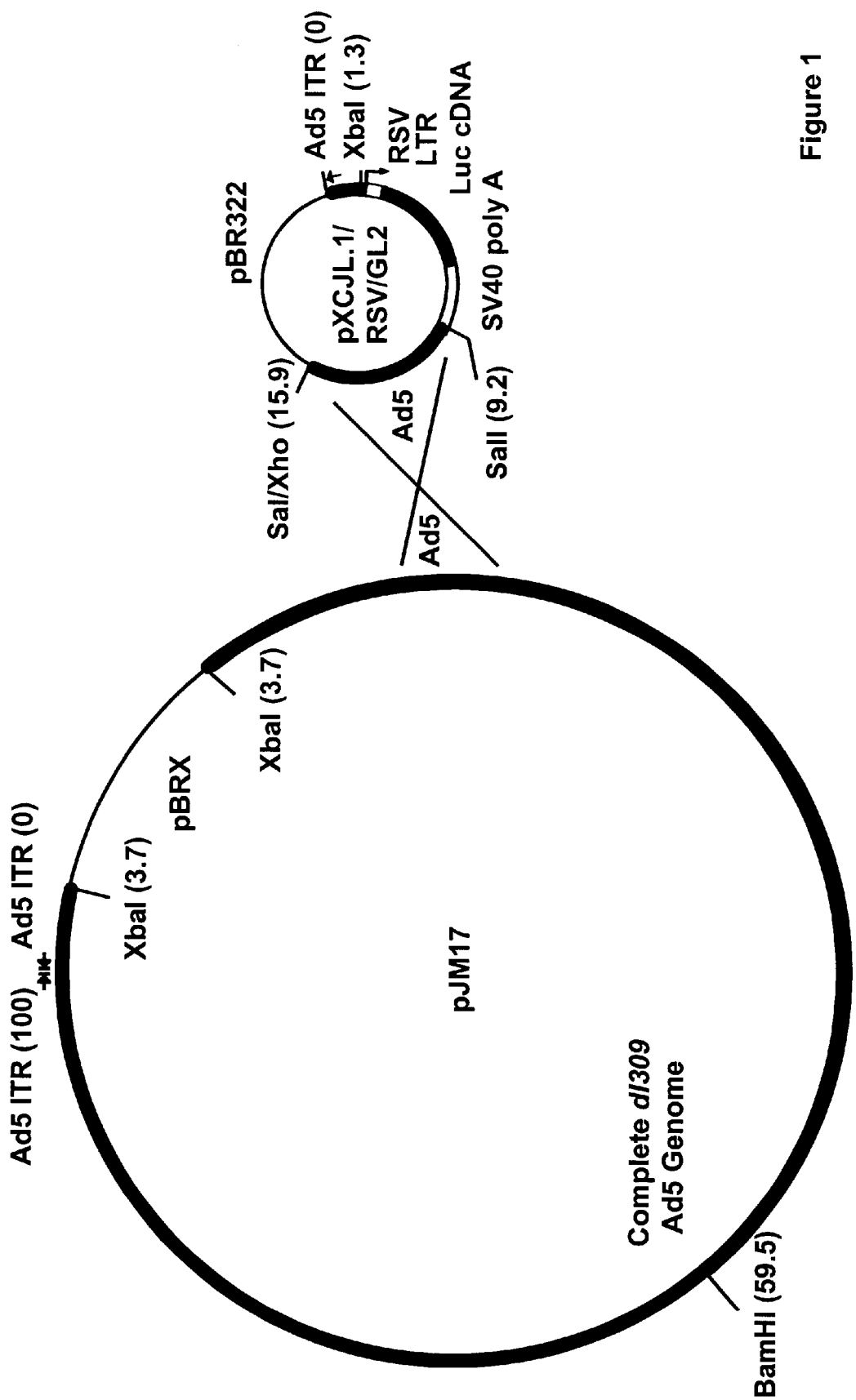
FIG. 1 shows a representation of the construction of an adenoviral vector carrying the luciferase gene. The small plasmid at right carries the luciferase reporter gene embedded in sequences from the left end of the adenovirus type 5 genome, while the larger plasmid at left carries the complete dl309 adenovirus type 5 genome. The "x" between the two plasaids represents the homologous crossover event which generates the desired recombinant virus forllowing the cotransfection of perissive 293 host cells.

SUMMARY OF THE INVENTION:

The invention concerns therapeutic agents for the prevention and treatient of cardiovascular disease. More specifically, the invention relates to modified viruses, especially adenoviruses, that carry gene sequences capable of ameliorating or preventing the symptoms of cardiovascular disease. It further relates to the use of such modified viruses in a genetic therapy for cardiovascular disease.

In detail, the invention provides a method of genetic therapy for the treatment of cardiovascular disease, wherein the method comprises providing an effective amount of a gene transfer vector to a somatic cell of an animal, the vector comprising a therapeutic gene sequence and being sufficient to mediate efficient gene transfer.

The invention further concerns the embodiment wherein the gene transfer vector is derived from adenovirus Subgenus C.

The invention further concerns the embodiment wherein the gene transfer vector is a complex derived from two or more of the following components or their derivatives: DNA, protein, cationic polymer, cationic lipid, and/or synthetic molecules, and in particular, the sub-embodiment wherein the protein-based and/or synthetic molecules of the gene transfer vector provide at least one of the following functions: i) plasma membrane penetration (by membrane fusion or endocytosis), ii) escape from lysosomal degradation (preferably by endosomal avoidance or disruption), iii) nuclear transport (preferably by virtue of a nuclear localization sequence), and iv) persistent nuclear retention (preferably by resistance to nuclease activity or by providing for replication).

The invention further concerns the above embodiments wherein the structure of the complex is maintained by ionic interactions between the anionic DNA-based component and (cationic polymers and/or cationic lipids) or wherein the proteins and/or synthetic molecules are chemically conjugated with a cationic polymer to maintain interaction with the DNA-based component or wherein the proteins and/or synthetic molecules are incorporated into liposomes (or liposomal complexes) of cationic lipids in order to maintain association with the DNA-based component.

The invention particularly concerns the embodiments, wherein the vascular cell is a smooth muscle cell, an endothelial cell, an immune cell, a cardiomyocyte or a cardiac fibroblast or wherein the cardiovascular disease is restenosis, atherosclerosis or dyslipidemia or involves inflammation, thrombosis, ischemia, myocardial infarction, reperfusion injury, or the immunological rejection of transplanted organs or tissues.

The invention also concerns the embodiment wherein the therapeutic gene sequence is expressed by the vascular cell, or secreted by the vascular cell, or is arrayed as a cell surface receptor by the vascular cell, and particularly wherein the therapeutic gene sequence encodes a receptor, receptor antagonist, a soluble receptor, or a receptor protein, containing a dominant-negative mutation.

The invention also concerns the embodiment wherein the therapeutic gene sequence is selected from the group consisting of Thrombin inhibitors (factor Xa antagonists, hirudin, thrombomodulin, antithrombin III, protein C, protein S, lipoprotein-associated coagulation inhibitor), Platelet inhibitors (RGD peptides, GP IIb/IIIa receptor antagonists), GF inhibitors (calcitonin gene-related peptide, somatostatin, soluble growth factor receptors, dominant-negative receptors, receptor antagonists), Antioxidants (superoxide dismutase, catalase, glutathione peroxidase), Antiproliferative proteins (tyrosine phosphatase, γ interferon, p53, eIF-2 kinase), Chimeric toxins (FGF-saporin, EGF-diphtheria toxin, TGFα-pseudomonas exotoxin A), Anti-inflammatory agents, TGF, β, lipocortin, vasocortin, IL-10), Anti-lipemic agents (LDL receptor, ApoAl, phospholipases) and Antisense or Ribozyme RNAs targeted against: c-myc, c-myb, c-fos, c-jun,PCNA, tyrosine kinase receptors, nucleolar p120 protein, slow calcium channels, HNG-COA reductase, cholesterol acyltransferase, cholesterol ester transfer proteins, thromboxane synthase, thromboxane receptors, etc.

The invention also contemplates the embodiments wherein the effective amount of the vector is provided in vivo by a percutaneous, catheter-based delivery, or by direct intra-arterial injection or infusion, with or without surgical isolation of the vessel, or is provided ex vivo to a graft, and wherein the graft is then introduced into the animal.

The method can be performed prior to, simultaneously with or subsequent to angioplasty, or surgical procedure, and may comprise the administration of more than one therapeutic gene sequences to the animal. The method may additionally comprise administering to the animal an additional pharmacological agent(s) in conjunction with gene therapy.

DESCRIPTION OF THE PREFERRED EMBODIMENTS

I. Genetic Therapy for Cardiovascular Diseam

The present invention concerns the use of viral vectors to provide a gene therapy for cardiovascular disease. In particular, it provides vectors and methods for transferring genetic material into the somatic cells of animals, including humans in order to effect such genetic therapy. The somatic cells that are the recipients of the gene therapy include smooth muscle cells, cardiomyocytes, cardiac fibroblasts, endothelial cells (such as the cells that line the vasculature), hepatocytes, neuronal cells, and cells of the immune system (such as stem cells, leukocytes, etc.).

The present invention derives in part from the recognition that despite the fact that clinically useful gene therapy protocols for treating cardiovascular disease have not heretofore been developed, such diseases are particularly amenable to gene therapy since: (i) genes can be transferred directly into coronary arteries, (ii) a number of proteins have been shown to inhibit VSMC proliferation, and (iii) even a temporary inhibition of VSMC proliferation might be sufficient to limit the formation of restenotic lesions (Forrester, J. S. et al., *J Amer. Col. Cardiol.* 17:758–769 (1991)). In particular, it is desirable to be able to deliver genes directly into any of four types of coronary vessels: (i) normal coronaries, (ii) atherosclerotic coronaries, (iii) atherosclerotic coronaries injured by angioplasty balloons, and (iv) atherosclerotic coronaries in which intra-coronary stents have been deployed.

The "treatment" provided by the molecules and methods of the present invention may be either "prophylactic" or "therapeutic." A prophylactic treatment is one that is provided in advance of any symptom of cardiovascular disease in order to prevent or attenuate any subsequent onset of a symptom of such disease. A therapeutic treatment is one that is provided in response to the onset of a symptom of cardiovascular disease, and serves to attenuate an actual symptom of the disease.

As used herein, the term "disease" denotes genetic or acquired disease, as well as conditions or disorders that may or may not have a genetic component (such as, for example, myocardial infarction, aneurysm, atherosclerosis, etc.). In particular, the term "disease" includes trauma or injury that is incidental to surgery, or other treatment, such as incidental to angioplasty, or to the deployment of intracoronary stents, etc.

Any of an array of cardiovascular diseases are amenable to the gene therapy protocols of the present invention. one particularly preferred class of cardiovascular diseases and conditions that may be treated by the methods of the present invention is associated with a process of cellular migration. Such migration may, for example, comprise an inflammatory response, such as the migration of neutrophils, lymphocytes and other leukocytes to sites of inflammation. Alternatively, such migration may involve the movement of muscle cells to sites of injury as is observed in atheroscerosis and restenosis (either spontaneous, incident to myocardial infarction, or incident to surgical intervention, such as angioplasty). A second preferred class of diseases and conditions that can be treated by the methods of the present invention involve those that are associated with the endogenous expression of hormonal and other factors, such as growth hormone, growth factors, etc.

The present invention can therefore be employed in the treatment of hyperlipidemia (such as high cholesterol levels, etc.), hereditary myopathies, thrombosis, restenosis, ischemic heart disease, atherosclerosis, asthma; adult respiratory distress syndrome (ARDS) or multiple organ injury syndromes secondary to septicemia or trauma; reperfusion injury of myocardial or other tissues; acute glomerulonephritis; reactive arthritis; dermatoses with acute inflammatory components; acute purulent meningitis or other central nervous system inflammatory disorders; therral injury; hemodialysis; leukapheresis; ulcerative colitis; Crohn's disease; necrotizing enterocolitis; granulocyte transfusion associated syndromes; and cytokine-induced toxicity.

II. The Molecules of the Pre snt Invention

A. The Therapeutic Gene Sequences of the Present Invention

The invention accomplishes the treatment of such diseases by providing vectors and methods suitable for delivering "therapeutic gene sequences" to the somatic cells of patients. The particular therapeutic gene sequence used will vary depending on the condition that is to be treated, and the targeted somatic cell type. Thus, for example, muscle cells can be targeted with gene sequences that effect their ability to support the migration of smooth muscle cells in order to treat potential restenosis, etc., or leukocytes in order to treat inflammatory responses, etc. Neuronal cells can be targeted to receive sequences that would relieve cardiac conduction abnormalities.

The therapeutic gene sequences of the present invention can, and preferably will, encode therapeutic proteins and antisense RNAs and/or ribozymes. In an especially preferred sub-embodiment, the therapeutic gene sequences will direct the secretion of the therapeutic protein. In an alternative embodiment, the therapeutic gene sequences of the present invention may provide antisense RNA (European Patent Appln. Publn. Nos. 263,740; 335,451; and 329,882, PCT Appln. Publn. No. WO90/00624) or ribozyme to the target cell in order to repress or prevent the expression of an endogenous gene sequence.

The transcription of the therapeutic gene sequences of the invention can be mediated from any suitable eucaryotic promoter. Examples of such suitable promoters include the RSV LTR, the SV40 early promoter, the cytomegalovirus (CMV) IE promoter, and the MMTV promoter. The SV40 promoter appears to be less active than the RSV LTR following transfection of cultured coronary VSNC. The CMV promoter appears to be stronger than the RSV LTR. Analysis of a luciferase vector driven by the smooth muscle α-actin promoter has suggested that it is nearly inactive in cultured coronary VSMC.

The nature of the therapeutic gene sequence employed, and whether that sequence is to be expressed and/or secreted will depend upon the particular disease or condition that is to be treated. As indicated, the expression of these molecules can be depressed by antisense expression, however, it is more preferable to employ therapeutic gene sequences that direct the secretion of proteins that are antagonists of inflammatory mediators or proliferation or migration processes. Examples of such therapeutic gene sequences are those that encode Thrombin inhibitors (factor Xa antagonists, hirudin, thrombomodulin, antithrombin III, protein C, protein S, lipoprotein-associated coagulation inhibitor), Platelet inhibitors (RGD peptides, GP IIb/IIha receptor antagonists), GF inhibitors (calcitonin gene-related peptide, somatostatin, soluble growth factor receptors, dominant-negative receptors, receptor antagonists), Antioxidants (superoxide dismutase, catalase, glutathione peroxidase), Antiproliferative proteins (tyrosine phosphatase, γ-interferon, p53, elF-2 kinase), Chimeric toxins (FGF-saporin, EGF-diphtheria toxin, TGFα-pseudomonas exotoxin A), Anti-inflammatory agents, TGFβ, lipocortin, vasocortin, IL-10), Anti-lipemic agents (LDL receptor, ApoA1, phospholipases) and Antisense or Ribozyme RNAs targeted against: c-myc, c-myb, c-fos, c-jun,PCNA, tyrosine kinase receptors, nucleolar p120 protein, slow calcium channels, HKG-CoA reductase, cholesterol acyltransferase, cholesterol ester transfer proteins, thromboxane synthase, thromboxane receptors, etc. The strategy behind this approach derives from the fact that only a subset of the vascular cells will express therapeutic genes after gene transfer. In order to facilitate the proper processing of the natural propeptide sequences by the vascular smooth muscle cells, it may be desirable to link the therapeutic gene sequences to gene sequences encoding signal peptides known to be efficiently processed by vascular cells (such as those from collagen or lysyl oxidase).

The secretion of therapeutic gene products from a modest population of infected vascular cells will create a microenvironment around the lesion which contains a high concentration of antiproliferative proteins. For example, locally-produced, persistent high concentrations of γ-interferon, somatostatin, etc., will inhibit VSMC proliferation and thus prevent or lessen restenosis.

In a second sub-embodiment, the therapeutic gene sequences will direct the secretion of the therapeutic protein that is a "soluble receptor" (i.e. a fragment of a receptor molecule that retains its ligand binding capacity, but is secreted from the cell into the circulation, or intercellular fluid). This approach, referred to as a "soluble receptor strategy," will enable a relatively small number of genetically reprogrammed cells to protect their neighbors from proliferative stimuli by secreting soluble receptors which will bind and thus inactivate specific growth factors. Examples of suitable receptors that may be solubilized include the PDGF α- and β-receptors, the TGF α- and β-receptors, receptors for the acidic and basic forms of FGF, EGF receptors, thrombin receptors, interleukin receptors, macrophage colony stimulating factor receptors, and TNF-α receptors, as well as soluble ICAMS, VCAMS, soluble selectins, etc.

In a third sub-embodiment, the therapeutic gene sequences will direct the expression of the therapeutic protein and its insertion into the target cell membrane, so as to create a receptor molecule on the target cell that would be capable of contacting extracellular molecules or ligands. These recombinant receptors may be used to increase cellular responsiveness to endogenous growth inhibitors. Alternatively, these recombinant receptors may be designed so as to transmit a growth regulatory signal in response to the administration of an exogenous substance. In this manner, the neointimal growth rate can be precisely controlled by systemic administration of the exogenous substance.

In a fourth sub-embodiment, the therapeutic gene sequences will direct the expression of growth factor receptors which have been mutated or truncated so that they are no longer capable of signal transduction. For example, the deletion or mutation of the tyrosine kinase domain in a growth factor receptor cDNA will result in a protein which is capable of dimerization (or multimerization) and ligand binding; however, ligand binding will not lead to signal transduction due to the lack of a functional kinase domain. Defective receptors that have such characteristics are referred to as dominant-negative receptors, because the incorporation of one mutant receptor can inactivate a larger multieeric complex, so that the negative effect of the mutant receptor can dominate over the wild-type binding partner(s)

1. Adenovirus-mediated Gene Therapy for Atherosclerosis

The preferred gene therapy for atherosclerosis derives in part from an appreciation of the molecular machinery for lipid metabolism and the existence of single-gene disorders such as LDL receptor deficiency that are especially propitious candidates for gene therapy in somatic cells. Factors which favor LDL receptor deficiency as a priority for gene therapy research include extraordinarily efficient uptake of adenovirus by liver even with systemic injection, the opportunity for portal vein injection of virus or engineered cells, the likelihood that relatively broad ranges in the levels of gene expression will be tolerated, the early lethality resulting from LDL receptor mutations, and the potential implications for augmenting LDL receptor abundance in more common forms of hyperlipidemia.

A reciprocal strategy to protect against or reverse atherosclerosis is based on augmentation of circulating HDL cholesterol: in mice, intravenous injection of recombinant adenovirus encoding human apolipoprotein A1 results in overexpression of ApoA1 and, consequently, increasing HDL cholesterol to levels that are known to be protective in humans. ApoA1, like other secreted, circulating proteins, is particularly amenable to a gene transfer strategy, since virtual any somatic cell (particularly hepatic cells) could be targeted to serve as a source of the gene product.

2. Adenovirus-nadiated Gone Therapy for Hereditary Ryopathies

Gene delivery to muscle itself will be required for Duchenne (DMD) and Becker muscular dystrophies: X-linked disorders caused by absence or abnormalities, respectively, of the sarcolemmal protein, dystrophin. Myoblast transfer and direct injection of plasmids encoding dystrophin have been employed in efforts to restore dystrophin expression in DMD patients or dystrophin-deficient mdx mice, yet daunting limitations are inherent to both techniques that rely on local injection, i.e. the total mass of skeletal muscle needing correction, the distribution and inaccessibility of respiratory muscles on which the clinical outcome largely depends, the concurrent need to restore dystrophin expression in myocardium, and the meager production of dystrophin-positive muscle fibers.

In contrast, mouse skeletal muscle that had been injected with adenovirus encoding the *E. coli* β-galactosidase marker gene (lacZ) labeled more extensive muscle segments than did plasmid injection. Indeed, adenovirus was at least 10-fold more efficient than naked DNA for conferring expression of dystrophin to mdx mice. of note, however, some therapeutic gene sequences, such as dystrophin are quite large (14,000 bp) and substantially exceed the present (7,500 bp) capacity of adenovirus vectors. Thus, for such therapies, truncated molecules (such as the 6,300 bp "minidystrophin" cDNA, derived from a Becker patient with phenotypically mild deletion are preferably employed. In this circumstance, even the truncated protein was sufficient for appropriate in vivo localization. It is possible that patients suffering from more severe deletions may not fully respond to adenoviral delivery of minidystrophin.

As demonstrated in Example 8 below, cardiac muscle can be targeted at high efficiency and specificity by simple intra-arterial injection. Skeletal muscle can also be targeted at lower efficiency and specificity by simple intraperitoneal injection. Nonetheless, muscle-specific regulatory sequences and even elements that discriminate between cardiac and skeletal muscle may be used, to direct tissue-specific expression of recombinant adenoviral genes in clinical settings where local delivery would be problematic.

3. Adenovirus-mediated Gene Therapy for Coronary Artery Restenosis and Thrombosis As indicated above, adenovirus-mediated gene therapy is particularly well-suited as an adjunct to coronary angioplasty, since even temporary inhibition of smooth muscle cell proliferation might suffice to limit formation of restenoic lesions that confound the clinical outcome of this procedure. Furthermore, although numerous pharmacological agents inhibit restenosis in rodent models, these approaches have largely failed when attempted in large mammals or in clinical trials. As this failure could be due in part to the inability of large mammals (including humans) to tolerate the high systemic doses used in rodent models, local delivery catheters might be employed to deliver high-dose therapy locally to the susceptible coronary artery in conjunction with cardiac catherization or angioplasty. However, many recombinant pharmaceuticals are prohibitively expensive for chronic treatment, and there are formidable technical challenges to maintaining high local drug doses in coronary vessels for days to weeks after a single transcatheter infusion. Gene therapy, by contrast, is particularly well suited to these challenges, since this approach would generally reprogram the coronary vessel, to produce the necessary recombinant proteins for the requisite period of time. As indicated below, such gene therapy can be employed in concert with the above-discussed pharmacological treatments.

The concept of direct gene transfer to inhibit restenosis was first articulated in the context of retrovirus- and Lipofectin™-mediated gene transfer (Nabel, E. G. et al., *Science* 249:1285 (1990). However, the absolute level of recombinant protein produced in vivo by these techniques was far below that which would be considered therapeutically significant.

Apart from the need for more efficient gene transfer, methods were required that would be applicable to atherosclerotic vessels as well. The potential efficiency for adenovirus-mediated gene transfer to the vasculature In viva is supported strongly by in vitro cell culture studies: coronary smooth muscle cells of canine, porcine, and human origin have been infected with efficiencies approaching 100%. Nanogram amounts of recombinant gene product can be recovered from a single 35 mm cell culture plate as early as 24 hours following infection. Successful gene transfer into virtually each cell on a culture plate represents a remarkable improvement over conventional transfection techniques (calcium-phosphate precipitation, retroviral transduction, Lipofectin™, DEAE-dextran, electroporation), which typically modify fewer than 10% of treated cells.

Recombinant adenovirus is an efficient vector for in v gene transfer and can be preferentially directed at vascular endothelium or smooth muscle cells. Recombinant adenoviral vectors have also been applied to the peripheral vessels of sheep (Le archand, P. et al., *Circ. Res.* 72:1132–1138 (1993)) and rabbits (Willard, J. E., et al., *Circulation* 86:I-473 (1992)), targeting the endothelium and intimal smooth muscle, respectively, in intact or denuded vessels. Transcatheter delivery has been shown to be feasible for targeting adenoviral vectors to rabbit coronary arteries and even myocardium (Barr, E. et al., *J Cell. Bioches.* 17D:195 (1993), herein incorporated by reference).

Suitable sources of therapeutic cDNA or gene sequences are abundant in the literature. Thrombin inhibitors (factor Xa antagonists (Dunwiddie, C. T. et al., *Biochem.* 31:12126–12131 (1992)), hirudin (Degryse, E. et al., *Prot. Engineer,* 2:459–465 (1989)), thrombomodulin (Wen, D. Z. et al., *Biochem.* 26:4350–4357 (1987)), antithrombin III (Gillespie, L. S. et al., *J. Biol. Chem.* 26:3995–4001 (1991)), protein C (Foster, D. C. et al., *Biochem,* 26:7003–7011 (1987)), protein S (Chang, G. T. et al., *Thromb. Haemost.* 67:526–532 (1992)), lipoprotein-associated coagulation inhibitor (Girard, T. J. et al., *Thromb. Res.* 55:37–50 (1989)), Platelet inhibitors (RGD peptides (Dennis, M. S. et al., *Proteins* 15:312–321 (1993)), GP IIb/IIIa receptor antagonists (Chang, H. H. et al., *Biochem. Bioghys. Res. Commun.* 190:242–249 (1993)), GF inhibitors (calcitonin gene-related peptide (Noel, M. et al., *J. Endocrinol. Invest.* 13:567–573 (1990)), somatostatin (Shen., L. P. et al., *Proc. Natl. Acad. Sci. (U.S.A.)* 79:4575–4579 (1982)), soluble growth tactor receptors (Duan, D. S. g al., *J. Biol. Chem.* 266:413–418 (1991)), dominant-negative receptors (Amaya, E. et al., *Cell* 66:257–270 (1991)), receptor antagonists (Baird, A. et al., *Proc. Natl. Acad. Sci. (U.S.A.)* 85:2324–2328 (1988)), Antioxidants (superoxide disiutase (Ho, Y. -S. et al., *FEBS Lett.* 229:256–260 (1988)), catalase (Furuta, S. et al., *J. Biochem (Tok)* 107:708–713 (1990)), glutathione peroxidase (Ho, Y. -S. et al., *FEBS lett,* 301:5–9 (1992)), Antiproliferative proteins (tyrosine phosphatase (Gu, M. et al., *Proc. Natl. Acad. Sci. (U.S.A.)* 89:2980–2984 (1992)), γ-interferon (Devos, R. et al., *Nucl. Acid. Res.* 10:2487–2501 (1982)), p53 (Zakut-Houri, R. et al., *EMBO J.* 4:1251–1255 (1985)), elF-2 kinase (Meurs, E. et al., *Cell* 62:379–390 (1990)), Chimeric toxins (FGF-saporin (Lappi, D. A. et al., *Biochem. Bioehys. Res. Commun.* 160:917–923 (1989)), EGF-diphtheria toxin (Pickering, J. G. et al., *J. Clin. Invest.* 91:724–729 (1993)), TGFα-pseudozonas exotoxin A (Nesri, E. A. et al., *J. Biol. Chem.* 268:4853–4862 (1993)), Anti-inflamatory agents (TGFβ (Bourdrel, L. at al., *Prot. Express. Purif.* 4:130–140 (1993)), lipocortin (Frey, B. M. et al., *Biochem J.* 275:219–225 (1991)), vasocortin (Sautebin, L. et al. *Pharmacol. Res.* 25:1–12 (1992)), IL-10 (Goodman, R. E. et al., *Biochem. Biophys. Res. Commun.* 189:1–7 (1992)), Anti-lipidemic agents (LDL receptor (Herz, J. et al., *Proc. Natl. Acad. Sci. (U.S.A.)* 90:2812–2816 (1993)), ApoA1 (Kopfler, W. P. et al., *Clin. Res,* 41:P211A (1993)), phospholipases (Kanda, A. et al., *Biochim. Biophys. Acta.* 1171:1–10 (1992)) and antisense or ribozyme RNAs (targeted against: c-myc, c-myb (Sala, A. et al., *Proc. Natl. Acad. Sci. (U.S.A.)* 89:10415–10419 (1992)), c-fos or c-jun, PCNA (Smith, M. J. et al., *Blood* 79:2107–2115 (1992)), tyrosine kinase receptors, nucleolar p120 protein (Saijo, Y. et al., *Canc. Lett.* 68:95–104 (1993)), slow calcium channels, thrombospondin receptors (Silverstein, R. L. et al., *J. Biol. Chem,* 267:16607–16612 (1992)), HMG-CoA reductase, cholesterol acyltransferase, cholesterol ester transfer proteins, thromxane synthase, thromboxane receptors, etc.).

These therapeutic cDNAS can be incorporated into replication-deficient adenoviral vectors by the methods outlined in Section IIIB, Example 2 and diagrammed in FIG. 1. In one eloiment, molecular cloning methods are used to replace the luciferase cDNA in pXCJL.1/RSV/GL2 with the therapeutic cDNA to create an adenoviral shuttle vector carrying the therapeutic cDNA between the RSV promoter and the SV40 polyadenylation signal. Cotransfection of the 293 host cell line with this construction and the balance of the adenoviral genome (provided by pJM17) will produce the desired therapeutic virus by homologous recombination. Standard protocols found in published procedures can be used to isolate, plaque purify, and amplify the recombinant virus.

The procedure described above is intended to illustrate, but not to limit the present invention. For example, a proven expression cassette consisting of a minimum of a promoter, a therapeutic cDNA, and a polyadenylation signal can substitute for the luciferase expression cassette in pXCJL1/RSV/GL2, as any combination of 5'-end, therapeutic cDNA (or gene), and 3'-end are possible. Furthermore, alternative adenoviral cloning systems can be employed in which the therapeutic expression cassette is inserted elsewhere in the adenoviral genome (such as the E3 region). The replication-deficiency of such a virus would be maintained by the E1 deletion. Although the example detailed above describes expression cassettes which are less than about 5.5 kilobases long, longer inserts can be accommodated by deleting additional regions in the adenoviral genole. For example, deletion of both the E1 and E3 regions will accommodate inserts of up to about 7.5 kilobases in length. Insertions of up to 35 kilobases can be accommodated by adding the adenoviral inverted terminal repeats (ITRs) to the desired DNA fragment, then transfecting a host cell line which provides additional viral functions in trans, or transfecting host cells in the presence of a helper virus.

An additional gene therapy can be applied following difficult angioplasty cases (involving coronary dissection or thrombosis-prone arterial segments), cases of emergency (rescue) angioplasty, and other clinical scenarios where coronary thrombosis night pose a chronic threat. The threat of thrombosis could be substantially reduced for a period of weeks by including a procedure whereby an anti-thrombotic gene therapy (employing therapeutic gene sequences encoding t-PA, urokinase, etc.) is delivered via catheter directly upstream of the thro bus-prone segment, or directly to the segment itself (possibly in conjunction with tacking-down a coronary dissection).

4. Adenoviral Delivery to Cardiac Muscle Cells

Since the ventricular myocytes do not divide, retroviral vectors (which require host cell proliferation) cannot be employed. Adenoviruses, however, infect non-replicating cells, and exhibit a significant ability to mediate more extensive gene delivery in skeletal muscle than plasmid DNA. Thus, they are suitable for use in cardiac muscle gene therapy by direct or intravenous delivery. Moreover, recombinant adenovirus mediates remarkably uniform gene transfer to adult cardiac cells in culture. Adenovirus-mediated gene transfer to the adult ventricular myocardium has been demonstrated in vivo, by local injection or coronary artery infusion (Leinwand, L. A. et al., *J. Cell. Bioches.* 17D:193 (1993); Barr, E. et al., *J. Cell. Biochem.* 17D:195 (1993), both herein incorporated by reference).

Gene therapies to the myocardium include (but are not limited to) antioxidants (such as superoxide dismutase, catalase, and glutathione peroxidase) to protect against ischemia or reperfusion injury, angiogenic growth factors (such as acidic and basic FGF) to stimulate angiogenesis to ischemic zones of myocardium, growth factors to stimulate cellular proliferation in infarcted areas, and rejection inhibitors (such as CD8) to prevent immune rejection of transplanted hearts.

5. Adenovirus-mediated Gen Therapy for Inflamation

For the treatment of inflammatory disorders (such as reperfusion injury of myocardial or other tissues, etc.) suitable therapeutic gene sequences include those that encode antisense molecules or therapeutic proteins that can suppress the expression of ICAMs such as ICAM-1 or ICAM-2 (Rothlein et al., *J. Immunol.* 137:1270 (1986); European Patent Application Publication No. 289,949; Staunton, D. E. et al., *Cell* 52:925–933 (1988); Staunton, D. M. et al., *FASEB J.* 3:a446 (1989); which references are incorporated herein by reference), VCAN-1 (Hynes, R. O. *Cell* 48:549–554 (1987)) or selecting (such as L-selectin (also termed LECCAM-1, MEL-14, LAN-1, LECAM-1 or lymphocyte homing receptor); E-selectin (also known as endothelial leukocyte adhesion molecule-1 (ELAM-1"), or LECCAM-2); and P-selectin (also known as CD62, platelet activation dependent granule external membrane (PADGEN), LECCAM-3, or granule membrane protein-140 (GNP-140); see, Gallatin, N. W. et al., *Nature* 304:30–34 (1989); Lasky, L. A. et al., *Cell* 56:1045–1055 (1989); Siegelman, N. H. et al., *Proc. Natl. Acad. Sci. (U.S.A.)* 86:5562–5566 (1989); Tedder, T. F. et al., *J. Exper. Med.* 170:123–133 (1989); Bevilacqua, M. P. et al., *Science* 243:1160–1165 (1989); Bovilacqua, M. P. et al., *Proc. Natl. Acad. Sci. (U.S.A.)* 84:9238–9242 (1987); Luscinskas, F. W. et al., *J. Immunol.* 143:3318–3324 (1989); Pober, J. S. at al., *Lab. Invest.* 64:301–305 (1991)).

B. The Preferred Vectors of the Present Invention

As used herein, the term "vector" is intended to denote a nucleic acid molecule. Preferably, such vectors will include therapeutic gene sequences and viral or plasmid DNA. A gene transfer vector is a virus or synthetic complex that contains a therapeutic gene sequence, and is able to mediate the transfer of the gene sequence into a recipient cell. Most preferably, the vectors of the present invention are associated with, or contained in a carrier, which may be a liposomal complex, a viral particle, etc. In such a case, the vectors are referred to as liposomal vectors, or viral vectors.

Adenoviruses, especially modified adenoviruses, are the preferred viral vector for delivering the therapeutic gene sequences of the present invention. Adenoviruses are intermediate-sized DNA viruses with genomes consisting of linear double-stranded DNA molecules of approximately 36,000 bp. The virion is an icosahedron about 70 nm in diameter, consisting exclusively of protein and DNA. Adenoviruses have been isolated from a large number of different species (mammalian and fowl) and over 100 different serotypes have been reported, some 43 of them human. The human adenoviruses, particularly types 2, 5, and 12, have been the most extensively characterized, and these viruses have served as valuable tools in the study of the molecular biology of DNA replication, transcription, RNA processing, and protein synthesis in mammalian cells (for review, see, Ginsberg, H., "The Adenoviruses," Plenum Press, NY (1984); Berkner, K. L. et al., *Biotechnigues* 6:616–629 (1988)). The biology of adenoviruses is reviewed by Graham, F. L. et al. (In: *Methods in Molecular Biology: Gene Transfer and Expression Protocols,* E. J. Murray, Ed. (Humana Press, New Jersey, (1991), Vol. 7, chap. 11, pp. 109–128 herein incorporated by reference).

Adenoviruses have several salient advantages over other gene therapy vectors. The viral particle is relatively stable, and, in the case of serotypes commonly used as vectors to date, the viral genome does not undergo rearrangement at a high rate. Insertions of foreign genes are generally maintained without change through successive rounds of viral replication. The adenovirus genome is also relatively easy to manipulate by recombinant DNA techniques, and the virus replicates efficiently in permissive 293 host cells.

Unlike retroviral vectors, adenoviral vectors do not require host cell replication in order to achieve high-level expression. This is due to the fact that adenoviral DNA remains episonal and does not need to integrate into the host genome before becoming transcriptionally active. Thus, adenovirus extends the range of cells and tissues that might be amenable to genetic manipulation, including the principal potential targets for cardiovascular applications.

The key advantage to the use of adenoviral vectors is the dramatic efficiency with which they mediate gene transfer. This efficiency is primarily due to the molecular mechanisms by which adenovirus mediates membrane penetration, lysosomal escape, and nuclear entry (Marsh, M. et al., In: *Advances in Virus Research,* K. Maramorosch et al, Eds. (Academic Press, New York, 1989), vol. 36, p. 107–151, herein incorporated by reference). In contrast, Lipofectin™-DNA complexes are only efficient at achieving membrane fusion; the vast majority of the DNA is then degraded by the lysosomes, and very little DNA ever reaches the cellular nucleus. Adenoviral vectors carrying antiproliferative genes can be directly targeted to a defined site, such as a site of angioplasty using a perforated infusion catheter, thereby ensuring maximal gene expression at the precise site where it is required. Adenoviruses are equally effective in mediating gene transfer into human, porcine, and canine smooth muscle cells, and the kinetics of viral binding are such that even a brief exposure to adenovirus will result in significant levels of gene transfer.

Most preferably, a modified adenoviral vector will be used to deliver the therapeutic gene sequences. The most preferred adenoviral vector is one that is replication-deficient due to deletion of critical genes in the E1 region of the viral genome. Such vectors can only be propagated in cell lines such as the permissive 293 host cell line, which provides the necessary E1a and E1b gene products in trans (Graham, F. L. et al. (In: *Methods in Molecular Biology: Gene Transfer and Expression Protocols,* E. J. Murray, Ed. (Humana Press, New Jersey, (1991), Vol. 7, chap. 11, pp. 109–128). Whereas wild-type Ad5 (containing E1 genes, and competent for viral replication in cells) can be cytopathic within 6 to 48 hours, the deletion of the E1 genes in the replication-deficient Ad5 vectors of the present invention precludes cytopathy.

The absence of chromosomal integration means that the DNA from a replication-deficient adenovirus has a finite lifespan (several weeks or more) before it is ultimately degraded by host nucleases. Thus, it is ideally designed for the treatment of cardiovascular disorders such as restenosis, and other acute diseases and conditions. As shown below, the time course of recombinant gene expression from such adenoviral vectors matches the time frame necessary to deliver antiproliferative therapy in vivo. The gradual decline in expression which is observed after two weeks is actually advantageous, since the expression of antiproliferative proteins at later time points might be inappropriate for maintenance and integrity of the arterial wall.

The replication-deficient adenoviral vectors currently utilized for in vivo gone transfer are largely derived from adenovirus serotype 5 (Ad5), although a few contain elements from closely related serotypes. Wild-type Ad5 is an icosahedral, non-enveloped virus carrying a linear, double-stranded 36 kilobase DNA genome. The molecular genetics and virology of Ad5 have been well characterized, so that much is known about Ad5 genes, their expression, and their function in viral replication (Ginsberg, H., "The Adenoviruses," Plenum Press, NY (1984)). For the cardiologist, the critical properties of Ad5 are those which favor its use for gene transfer in vivo—the availability of replication-deficient derivatives, the comparative ease with which the Ad5 genome can be manipulated, the variety of methods for virus delivery, the efficiency for infecting mammalian cells, the high levels of recombinant protein expression which can be obtained, and the relative lack of cytotoxicity. Adenovirus can be concentrated to exceptionally high titers, exceeding $10^{10}$ pfu/ml, can be engineered to accommodate very large DNA inserts, and possesses a broad host range, enabling tests in diverse animal models of human disease. Finally, the DNA copy generated from a retrovirus's RNA genome becomes permanently and randomly integrated into some chromosomal site within infected cells, a process that can give rise to aberrant cell behavior. The adenoviral genome, by contrast, remains physically separate from host cell DNA (episomal), obviating this hazard of insertional mutagenesis. As additional merits regarding safety, human adenoviruses have not been associated with clinical malignancies and, indeed, live adenovirus vaccines have been administered to large numbers of subjects without ill effect. Replication-deficient adenoviral vectors have been used to mediate in vivo gene transfer into bronchial epithelium (Rosenfeld, M. A. et al., *Cell* 68:143–155 (1992)) and skeletal muscle (Quantin, B. et al., *Proc. Natl. Acad. Sci. (U.S.A.)* 89:2581–2584 (1992)).

In a particularly preferred embodiment, the adenoviral vectors will be further modified so as to carry ligands specific for receptors present on the desired target cells. Alternatively, synthetic vectors can be constructed from synthetic and/or recombinant products. The synthetic vectors would be constructed of: i) one or more recombinant DNA cassette(s) directing the expression of therapeutic gene sequencers) (preferably, but not necessarily in the form of plasmid(s)), ii) a ligand to mediate cell attachment and/or endocytosis (preferable a ligand which targets a specific cell or tissue), iii) a component for mediating escape from the lysosomal pathway (such as the hemagglutinin spike protein from the influenza virus), and iv) a nuclear localization signal (NLS) peptide or other mechanism for mediating transport to the nucleus. The high efficiency gene transfer provided by these methods is described in Example 8.

These components can be linked together by covalently attaching polycationic linkers (such as poly-L-lysine) to the non-DNA components, then mixing these linkered components with the DNA component(s) to form ionic complexes. Additionally or alternatively, labile covalent bonds can by utilized which will break under specific conditions (such as under low pH in lysosomes). Additionally or alternatively, liposomal complexes of cationic lipids (i.e. liposomes, or lipid-protein complexes) can be used to maintain association of the DNA-based components with the other functional components. Additionally, modifications can be made to the DNA-based component in order to prolong its expression in the nucleus. Such modifications include the chemical modification of the DNA in order to prevent its degradation, and/or providing a means of DNA replication, such as including the Epstein-Barr virus (EBV) origin of replication (ori-P) and the gene encoding EBV nuclear antigen 1 (EBNA-1)).

The capacity and efficiency of the vectors of the present invention to mediate gene therapy can be effectively demonstrated by incorporating a marker gene in place of the therapeutic gene sequence, and then determining the kinetics of marker gene expression in the recipient patient. The luciferase reporter system is a preferred marker gene. Alternatively, since each reporter system has its own unique and useful properties, other marker genes may be employed. one feature of note in the luciferase reporter system is the short half-life of the protein in the call. Thus luciferase does not accumulate to high levels in vitro or in vivo due to its rapid turnover in cells. In contrast, the β-galactosidase gene product of the *E. coli* LacZ reporter gene is remarkably stable in eucaryotic cells. The histochemical X-gal stain for lacZ positive calls is compromised by cells within the arterial wall which express the mammalian β-galactosidase activity. This problem can be overcome by adding sequences encoding a nuclear localization signal (NLS) to the 5'-end of the *E. coli* LacZ gene. After transcription and translation of this fusion gene, the NMS directs transport of β-galactosidase to the nucleus. Following fixation and incubation with the X-gal substrate, the distinct nuclear staining will definitively identify the cells which carry the reporter gene. As predicted by their relative stabilities, we have found that β-galactosidase accumulates to higher levels than luciferase after gene transfer, both in vitro and in vivo. Thus the two reporter systems complement each other by indicating the range of gene expression that uight be expected from a therapeutic construction after gene transfer. The absolute levels of therapeutic gene expression obtained in vivo will depend upon a large nubber of variables including: DNA copy number, DNA stability, promoter strength, transcription rate, messenger RNA stability, translation rate, post-transnational modifications, and protein stability.

III. The Administration of the Nolecules of the Present Invention

The genetic therapy of the present invention can be administered in a variety of ways. In one embodiment, such therapy can be provided alone, i.e as the sole therapy administered to a patient. Alternatively, two or more different therapeutic gene sequences can be provided to a patient in a manner that results in overlapping expression of more than one introduced therapeutic gene sequence. For example, a patient can be administered a combination of therapeutic vectors that encode two or nore of the following therapeutic gene sequences: Thrombin inhibitors (factor Xa antagonists, hirudin, thrombomodulin, antithrombin III, protein C, protein S, lipoprotein-associated coagulation inhibitor), Platelet inhibitors (RGD peptides, GP IIb/IIIa receptor antagonists), GF inhibitors (calcitonin gene-related peptide, somatostatin, soluble growth factor receptors, doninant-negative receptors, receptor antagonists), Antioxidants (superoxide dismutase, catalase, glutathione peroxidase), Antiproliferative proteins (tyrosine phosphatase, γ-interforon, p53, elF-2 kinase), Chimeric toxins (FGF-saporin, EGF-diphtheria toxin, TGFα-pseudozonas exotoxin A), Anti-inflammatory agents, TGFβ, lipocortin, vasocortin, IL-10), Antilipemic agents (LDL receptor, ApoA1, phospholipases) and Antisense or Ribozyme RNAs targeted against: c-syc, c-myb, c-fos, c-jun,PCNA, tyrosine kinase receptors, nucleolar p120 protein, slow calcium channels, HMG-CoA reductase, cholesterol acyltransferase, cholesterol ester transfer proteins, thromboxane synthase, thromboxane receptors, etc. The combination of two or more different classes of therapeutic sequence, such as hirudin (a thrombin inhibitor) and γ-interferon (an antiproliferative), may effect a more potent or synergistic therapy for restenosis. Similarly, a gene therapy comprising sets of vectors that mediate the expression of a solubilized ICAM-1 and a solubilized selectin can be employed. In such combined vector therapies, the multiple therapeutic gene sequences can be present on the same introduced vector, or can be present on separate vectors since a combination of vectors can be delivered as easily as a single vector.

As indicated, the time course of the genetic therapy of the present invention commences within hours of administration, and lasts for several weeks or longer. In a preferred embodiment, such gene therapy can be used in combination with convention pharmacological therapies to effect a more potent or synergistic response. Thus, conventional anti-inflammatory agents, anti-restenoic agents, anti-thrombin factors, etc. can be used in combination with one or more of the therapeutic gene sequences of the present invention. The utility of combining such therapies lies in the complementarity in the intervals over which each of the therapies are effective. After administration, a pharmaceutical is generally effective for a period of hours, and is seldom effective for more than one day. Conversely, the genetic therapy of the present invention may take hours to become effective, and will continue to be effective over a period of time far in excess of that which can be obtained by pharmaceutical therapy.

A. In Vivo Administration

Any of a variety of methods can be used to provide the therapeutic vector molecules to a desired site. A desirable coronary delivery system has the general properties of being atraumatic, and permitting a prolonged contact of relatively small volumes with the arterial wall, while maintaining adequate distal perfusion.

In one emodiment, the therapeutic gene sequences are provided to a localized, preselected site using percutaneous catheter-based local delivery systems. One such device (the Wolinsky Infusion Catheter made by USCI) insures gene delivery to the vessel wall, but occasionally causes intra-mural hematomas and dissections that are grossly evident at three days post infusion. The severity of injury can be reduced by choosing appropriately sized balloons (balloon to artery ratio of 1:1) and lower infusion pressures (2–3 atmospheres). However, the kinetics of viral binding and the high efficiency of gene transfer afforded by adenoviral vectors decreases any need for high pressure delivery, and enables adequate levels of gene expression to be achieved with sustained, low pressure infusions which should not impose significant arterial damage.

In lieu of using such catheters, other catheter designs may be employed including: i) microporous balloons (made of dialysis-like membranes of defined porosity which allow the infusate to seep out rather than jet out), ii) hydrogel-coated balloons (in which the therapeutic component is incorporated into the hydrogel for distribution into the arterial wall), iii) dual balloons (with infusion port between the two balloons), iv) double-balloons (with one balloon inside a second perforated or microporous balloon), v) channel balloons (in which the distribution of the therapeutic agent is compartmentalized), and vi) seeded balloons (in which inflation causes the rupture of "seeds" which release therapeutic reagents into the vascular wall).

Gene expression can preferentially be targeted to the lusinal surface of the artery by low-pressure, dual-balloon delivery; or to the deeper layers in the artery by high-pressure, Wolinsky balloon delivery. Thus the catheter delivery device, as well as the manner in which it is employed, can be used to select and determine the cellular populations which are most likely to receive the recombinant genes.

In an alternative embodiment, the therapeutic gene sequences are provided to a localized, preselected site using an implanted stent, graft or implant, that is introduced into the desired site, as by interventional or surgical procedures, etc. Control release preparations may be achieved through the use of polymers to complex or absorb the adenoviral vectors. The controlled delivery may be exercised by selecting appropriate macromolecules (for example polyesters, polyamino acids, polyvinyl, pyrrolidone, ethylenevinylacetate, methylcellulose, carboxymethylcellulose, or protazine sulfate) and the concentration of macromolecules as well as the methods of incorporation in order to control release. Another possible method to control the duration of action by controlled release preparations is to incorporate the adenoviral vectors into particles of a polymeric material such as polyesters, polyamino acids, hydrogels, poly(lactic acid) or ethylene vinylacetate copolymers. Alternatively, instead of incorporating these vectors into polymeric particles, it is possible to entrap these materials in, for example, hydroxyzethylcellulose, gelatin, etc. Such techniques are disclosed in Remington's Pharmaceutical Sciences (1980).

B. Ex vivo Administration

In an alternative embodiment, the vectors of the present invention may be provided to patients using an AN vivo regimen. This ex-vivo approach to targeting gene therapy to a particular organ, tissue, and/or cell population has a unique advantage since the organ/tissue/cell can be subjected for extended periods of time to high concentrations of gene transfer vector resulting in high-efficiency gene transfer. For example, vascular grafts such as saphonous veins or mammary arteries can be treated with the gene transfer vectors elaborated herein between the explantation and implantation procedures to prevent the accelerated atherosclerosis and restenosis which confounds autologous vascular graft transplantations such as coronary artery bypass grafts. A second application is in the field of cardiac transplantation, where the explanted heart could be bathed in a cardioplegic solution containing a gene transfer vector which prevents transplant rejection (such as by expressing CD8 to inhibit allospecific T-cell responders, etc.) or which mediates against ischesic and/or reperfusion injury (by directing the expression of antioxidants including superoxide dismutase, catalase, glutathione peroxidase, etc.). A third ex-vivo example involves liver transplantation. In this case, an explanted liver destined for transplantation into a hyperlipidemic person could be modified with the gene transfer vectors described herein to produce additional LDL receptors and/or apolipoprotein A1, etc. The examples detailed above are utilized for illustrative purposes and should in no way limit the general approach of genetically modifying explanted organs/tissues/cells before implantation into the patient. In some cases, it may even be desirable to explant organs/tissues/cells solely for the purpose of obtaining high-efficiency gene transfer before replacing them back into the same patient.

Having now generally described the invention, the same will be more readily understood through reference to the following examples which are provided by way of illustration, and are not intended to be limiting of the present invention, unless specified.

Example 1

Direct In Vivo Gene Transfer

Influences of Delivery Volume and Pressure

In order to evaluate the basic parameters which influence the efficiency of direct gene transfer, a perforated balloon delivery system (Wolinsky Infusion Catheter [WIC], USCI, Billerica, Ma.) was employed. 50 µg of reporter vector DNA (pRSVL) was complexed with 150 µg of Lipofectin™ (BRL, Gaithersburg, Md.) and diluted to either 4 or 8 ml with Opti-MEM I® (also from BRL). The volumes were infused into the RCA, LAD, and LCX coronary arteries of 8 intubated Hanford miniature swine using modestly oversized WIC's (balloon/artery ratio of 1.1–1.3) and inflation pressures of either 4 or 8 atm. The animals were revived following catheterization and maintained for 3 days before sacrifice for arterial harvest and luciferase assay using a Monolight 2010 luminometer (Analytical Luminescence Laboratory [ALL], San diego, Calif.). Background was subtracted and the total mass of luciferase protein recovered from each artery was calculated after calibration of the luminometer using certified luciferase standards (ALL). Luciferase activity corresponding to a ≧3 fg protein was detected in 23 of 24 arteries (96%) with a mean of 283 fg luciferase recovered per infused artery. The results of varying the DNA concentrations and balloon pressures are shown in Table 1, where each value in the 2×2 matrix gives the mean femtograms (fg) of active luciferase recovered from 6 arteries (2 RCAs, 2 LADS, 2 LCXS) ±standard deviation.

TABLE 1

EFFECT OF VOLUME AND PRESSURE

|      | 4 atm    | 8 atm    |
|------|----------|----------|
| 8 ml | 43 ± 44  | 148 ± 155 |
| 4 ml | 216 ± 368 | 771 ± 937 |

Thus, using equal amounts of reporter vector, both the higher DNA concentration (4 vs 8 ml delivery volume), and the higher infusion pressure (8 vs 4 atmospheres) resulted in more efficient gene transfer, with maximum transfer achieved when these two parameters were combined.

Example 2

Construction of an Adenoviral Reporter Vector Carrying the Luciferase Gene

The lacZ reporter gene has been employed in direct gene transfer experiments targeting peripheral (Nabel, E. G. et al., *Science* 249:1285 (1990); Flugelman, M. Y. et al., *Circulation* 85:1110–1117 (1992); Lemarchand, P. et al., *Circ. Res.* 72:1132–1138 (1993)) and coronary arteries (Lim, C. S. et al., *Circulation* 83:2007–2011 (1991)), but endogenous β-galactosidase activity has been observed in arterial sections by our laboratory and others (Lim, C. S. et al., *Circulation* 83:2007–2011 (1991); Flugelman, M. Y. et al., *Circulation* 85:1110 (1992)). For this reason, the luciferase reporter system was used to accurately quantitate levels of recombinant protein produced in coronary arteries following direct gene transfer.

Early experiments employed complexes of Lipofectin™ (a 1:1 (w/w) liposome formulation of a cationic lipid and dioleoyl phosphatidylethanolamine obtained from BRL; Gaithersburg, Md.) and a reporter plasmid (pRSVL) which carries the long terminal repeat of the Rous sarcoma virus, the firefly luciferase cDNA, and the SV40 small-t intron/polyadenylation signal (Keller, G. A. et al., *Proc. Natl. Acad. Sci.* (*U.S.A.*) 11:3264–3268 (1987)). The inclusion of 1 mg/ml bovine serum albumin (BSA) in the Lipofectin™ cocktail results in higher and more reproducible results, presumably because it acts as a carrier and thus prevents the DNA-Lipofectin™ complexes from adhering to the plastic tubes, pipettes and catheters. The addition of influenza hemagglutinin protein (HA) yields results that are similar to those obtained with BSA. However, combining HA with BSA in the transection cocktail failed to yield further improvements in gene transfer. Because sub-physiological levels of recombinant gene expression were obtained using Lipofectin™, a replication-deficient adenoviral vector carrying an analogous expression cassette was constructed (FIG. 1).

As shown in FIG. 1, the adenoviral vector carrying the luciferase gene was derived using the replication-deficient adenovirus type 5 (Ad5) cloning system of F. L. Graham (McGrory, W. J. et al., *Virol.* 163:614–617 (1988), herein incorporated by reference). Briefly, a firefly luciferase expression cassette analogous to the one in pRSVL (Keller, G. A. et al., *Proc. Natl. Acad. Sci.* (*U.S.A.*) 84:3264–3268 (1987), herein incorporated by reference) was subcloned between left-end adenoviral sequences in pXCJL.1 to create pXCJL.1/RSV/GL2. This construction was cotransfected into the transformed 293 embryonic kidney cell line (Graham, F. L. et al., *J. Gen. Virol.* 36:59–72 (1977)) with a plasid (pJM17) which carries a circularized dl309 adenoviral genome (McGrory, W. J. et al., *Virol.* 163:614–617 (1988)), herein incorporated by reference). The presence of both the PBR322 derivative (pBRX) and adenoviral genone within pJX17 causes this plasaid to exceed viral packaging constraints and provides a selection for the rescue of shorter recombinants. Following cotransfection of 293 cells, spontaneous homologous recombination between the two plasmids (pJM17 and pXCJL.1/RSV/GL2) and linearization mediated by Ad5 inverted terminal repeats (ITRs) generated a virus (Ad5/RSV/GL2) with a substitution of the luciferase expression cassette for the adenoviral E1 genes. The deletion of the E1 genes renders the adenovirus replication-deficient in all calls other than the permissive 293 host which provides E1 functions in trans.

Putative viral clones were plaque purified, screened for the presence of the luciferase gene insert, propagated, isolated and titered according to the protocols of Graham, F. L. et al. (In: *Methods in Molecular Biolog: Gene Transfer and Exoression Protocols,* E. J. Murray, Ed. (Humana Press, New Jersey, (1991), Vol. 7, chap. 11, pp. 109–128).

Example 3

Comparative Efficiency of Lipofectin™- vs. Adenovirus-mediated Gene Transfer To further characterize the comparative efficiency of replication-deficient adenoviral vectors vs Lipofectin™ at mediating direct gene transfer into living coronary arteries, 50 µg of reporter vector DNA (pCMVβ, in which the CNV promoter drove the expression of the *E. coli* LacZ gene; or pRSVL, in which the long terminal repeat (LTR) from the Rous sarcoma virus (RSV) drove the expression of the firefly luciferase cDNA) was complexed with 150 µg of Lipofectin™ (BRL) and diluted to 4 ml with Opti-MEN I (BRL).

Viral infections were performed with 4 ml dilutions of recombinant adenoviruses harboring analogous expression cassettes: $5\times10^9$ pfu per artery of Ad5/HCMV/LacZ (in which LacZ is expressed from the CMV promoter; vector obtained from A. Bett and F. L. Graham) or $4\times10^9$ pfu per artery of Ad5/RSV/GL2 (in which the luciferase gene is expressed from the RSV LTR). Under fluoroscopy, these solutions were infused at a pressure of 8 atmospheres into the coronary arteries of intubated Hanford miniature swine using perforated balloon catheters. Levels of reporter gene activity were determined 3 days following infusion catheterization using a chemiluminescent assay for β-galactosidase and a luminescent assay for luciferase. The results of this comparison are shown in Table 2, where each value in the 2×2 matrix represents the mean amount of reporter gene product recovered from 3 to 6 coronary arteries ± standard deviation.

TABLE 2

COMPARATIVE EXPRESSION EFFICIENCY

| Reporter Protein | β-galactosidase (ng) | Luciferase (pg) |
| --- | --- | --- |
| Lipofectin ™ | 1.52 ± 0.68 | 0.11 ± 0.10 |
| Adenovirus | 106 ± 96 | 35.9 ± 27.7 |

Thus, with both reporter systems, markedly higher levels of recombinant gene product were obtained from adenoviral vectors than from Lipofections using 50 μg of highly purified plasmid DNA. The absolute amounts of recombinant gene product obtained were obviously dependent upon the mass of DNA (or titer of virus) employed; nevertheless, this study demonstrated that when equal volumes were infused, replication-deficient adenoviral vectors were far more efficient than Lipofectin™ at mediating direct gene transfer into living coronary arteries. A 70-fold difference was observed using the LacZ reporter gene, and a 240-fold difference was observed using luciferase. It is interesting to note that the nanogram levels of β-galactosidase were far in excess of the picogram levels of luciferase. Most of this difference is probably due to the high stability of the β-galactosidase protein relative to luciferase, although promoter strength may also be a contributing factor. Nevertheless, both reporter systems demonstrate the clear superiority of adenoviral vectors over more conventional methods of gene transfer.

Example 4

Direct Gene Transfer by Adenoviral Vectors

Time Course of Therapeutic Gene Sequence Expression

Multiple lines of evidence, from animal models as well as human autopsies, indicate that the majority of the smooth muscle cell migration and proliferation responsible for restenosis occur during the first two weeks following coronary angioplasty. Thus in order to be most effective, an antiproliferative gene therapy directed against restenosis would have to provide for at least two weeks of recombinant gene expression. It was therefore important to determine if the duration of recombinant gene expression provided by these vectors makes them suitable for use in a genetic therapy, such as one against restenosis. Under fluoroscopy, a 4 ml volume containing $4\times10^9$ pfu of Ad5/RSV/GL2 was infused into each porcine coronary artery at a pressure of 8 atmospheres using a wolinsky catheter. Luciferase activity in the arteries was determined upon sacrifice at 1, 3, 7, and 14 days following catheterization. The results are reported in Table 3, where each value represents the mean picograms (pg) of active luciferase recovered from 3 to 6 coronary arteries ± standard deviation (sd).

TABLE 3

TIME COURSE OF EXPRESSION

| | Time From Infusion to Assay (Days) | | | |
| --- | --- | --- | --- | --- |
| | 1 | 3 | 7 | 14 |
| pg luciferase /artery ± 1 sd | 24 ± 23 | 27 ± 21 | 21 ± 39 | 12 ± 19 |
| No. of Coronaries Assayed | 3 | 6 | 6 | 6 |

The experiment indicates that similar levels of gene expression are obtained at 1, 3, 7, and 14 days following gene transfer, with a trend towards maximal expression at 3-days. Significantly, the results also indicate that gene expression could be detected after only a single day, indicating that gene therapy will have a therapeutic effect within 24 hours. Expression has been observed even at 28 days following gene transfer. This study provides strong evidence to suggest that the duration of gene expression provided by adenoviral vectors is suitable for antiproliferative gene therapies directed against coronary restenosis.

The luciferase assays three days after gene transfer further demonstrated that $4\times10^9$ plaque-forming units of recombinant virus produced at least 100-fold more luciferase than 50 μg of the analogous plasmid DNA-Lipofectin™ complex (Mazur, W. et al., *J. Cell. Biochem.* 17E:226 (1993), herein incorporated by reference). Comparable levels of recombinant gene expression were obtained in vivo as early as 24 hours after gene transfer, and expression persisted for at least 14 days (Ali, M. N. et ale, *Restenosis Summit V, May* 20–21, Cleveland, Ohio (1993), herein incorporated by reference). Thus, both the magnitude and duration of gone expression provided by recombinant adenoviruses appear suitable for the prevention of coronary restenosis.

Example 5

Direct Gene Transfer by Adenoviral Vectors

Efficiency of Expression in the Major Coronary Arteries

A comparison was made of Lipofectin™- and adenovirus-mediated gene transfer in all three major porcine coronary arteries: the circumflex (LCX), left anterior descending (LAD), and right coronary arteries (RCA). Male Hanford miniature swine weighing 50–100 lbs. at exsanguination were employed in a protocol which adhered to NIH and institutional guidelines.

Direct gene transfer into normal porcine coronary arteries was carried out under fluoroscopic guidance using a strictly percutaneous approach. All three major coronary arteries in each animal were subjected to gene transfer using wolinsky Infusion Catheters (USCI; Billerica, Mass.) oversized by 1.1–1.3 times the diameter of the target arterial segment. These catheters resemble conventional angioplasty devices except that the balloon is perforated with 28 microscopic holes (each 25 μm in diameter). The infusion balloon was positioned at the target site in each coronary, 4 ml of gene transfer reagent was loaded into the inflation device, and a pressure of 8 atmospheres was applied; resulting in simultaneous balloon inflation and gene infusion over a period of 12 to 28 seconds. For Lipofectin™ transfection of each coronary, 50 μg of pRSVL (Keller, G. A. et al., *Proc. Natl. Acad. Sci. (U.S.A.)* 84:3264–3268 (1987)) was couplexed with 150 μg of Lipofectin™ and diluted to a final volume of 4 ml with OptiMEM-I® (BRL). For each adenoviral infection, $4 \times 10^9$ plaque forming units of Ad5/RSV/GL2 (FIG. 1), were diluted to 4 ml with OptiMEM-I®.

Following gene transfer and angiography, the procedure was concluded and the swine were maintained for three days before being placed under deep anesthesia for exsanguination and analysis for luciferase expression. For such procedures, hearts were removed, placed in ice-cold PBS, and coronary arteries dissected from myocardium. The vessels were divided into multiple segments (each <1 cm long), minced, and homogenized in 100 μl of luciferase lysis reagent (25 mM Tris-phosphate, pH 7.8. 2 mM DTT, 2 mM 1,2-diaminocyclohexane-N,N,N',N'-tetraacetic acid, 10% glycerol, and 1% Triton X-100). The samples were centrifuged at 12,000 g for 5 minutes, and duplicate luciferase assays were performed with a Monolight 2010 luminometer (Analytical Luninescence Laboratory [ALL]; San Diego, Calif.). 100 μl of assay reagent (20 mM Tricine, pH 7.8, 1.07 mM $(MgCO_3)_4Mg(OH)_2 \cdot 5H_2O$, 2.67 mM $MgSO_4$, 0.1 mM EDTA, 33.3 am DTT, 270 μM coenzyme A, 470 μM luciferin, and 530 μM ATP) was added to each 20 μl sample of cleared supernatant and photons were counted for 30 seconds. Background values from vehicle-infused arteries (equivalent to background from lysis reagent) were subtracted and relative light units ware converted to mass units (pg) using calibration curves generated from parallel reactions performed with certified luciferase control standard (ALL).

Using these techniques, the efficiency of Lipofectin™- vs. adenovirus-mediated in vivo gene transfer was evaluated with respect to the type of coronary artery undergoing gene transfer. The total amounts of luciferase recovered from each vessel undergoing the two types of gene transfer are reported in picograms (pg) in Table 4 beneath the type of artery undergoing gene transfer: RCA, right coronary artery; LAD, left anterior descending; LCX, circumflex.

TABLE 4

| | NORMAL CORONARY ARTERIES | | |
|---|---|---|---|
| Animal # | RCA | LAD | LCX |
| | Transfected by Lipofectin ™ (pg) | | |
| 39 | 0.08 | 0.16 | 0.02 |
| 43 | 0.28 | 0.06 | 0.06 |
| | Infected by Adenovirus (pg) | | |
| 31 | 67.9 | 19.5 | 20.4 |
| 51 | 10.9 | 13.5 | 27.8 |

Variability in the levels of gene expression was observed using either Lipofectin™- or adenovirus-mediated gene transfer. In normal porcine coronary arteries, luciferase levels obtained with Lipofectin™ ranged from 0.02–0.28 pg, while levels obtained with the adenovirus ranged from 11–68 pg. Thus, the mean level of gene expression with adenovirus in the normal coronary arteries was 240 times higher than that achieved with Lipofectin™. The number of arteries of a certain type undergoing a particular gene transfer regimen is small (n=2), and the results are variable; nevertheless, it is also evident that adenovirus-mediated gene transfer yields similar results, regardless of the type of coronary artery targeted (RCA, LAD, or LCX).

The study summarized above was designed to compare the efficiency of Lipofectin™- versus adenovirus-mediated gene transfer when relatively small volumes (4 ml) containing average concentrations of DNA (or virus) were infused under identical conditions. The absolute levels of luciferase obtained from either gene transfer method can be improved by increasing the concentration of reporter gene or the volume of infusate. For example, Chapman, G. D. et al. (*Circ. Res.* 7:27–33 (1992)) achieved picogram levels of luciferase in canine coronary arteries using Lipofectin™ and similar percutaneous catheters, but the amounts of plasmid DNA (up to 650 μg) and the volumes of infusate (up to 20 ml) were far greater than those used here. Analogous strategies for adenoviral vectors (such as increased titer) should result in levels of luciferase production far higher than those reported here. Of importance to the long-term clinical application of such methods, adenovirus-mediated gene transfer was found to be comparably effective in normal and atherosclerotic arteries, and vessels subjected to balloon injury or stent deployment.

Example 6

Direct Gene Transfer into Atherosclerotic Coronary Arteries

The results in Table 4 demonstrate efficient gene transfer by the adenoviral vector into physiologically normal coronary arteries. Since the vascular targets for gene therapy against restenosis include atherosclerotic arteries and those displaying the pathology of VSMC hyperplasia, the efficiency of gene transfer was examined in three types of atherosclerotic porcine coronary arteries: uninjured, injured by oversized balloons, and injured by intracoronary stents (Table 5).

Hypercholesterolemia was induced with a high fat diet which produces predictable atherosclerotic changes in the coronary arteries (Pond, W. G., In: *Swine in Cardiovascular Research*, H. C. Stanton and H. J. Morsmann, Eds. (CRC Press, Florida, 1986), Vol, 2. chap. 1, herein incorporated by reference). The additional manipulations involving injury by oversized balloons (Schwartz, R. S. at al., *Circulation* 82:2190 (1990) herein incorporated by reference) or intracoronary stents (Rodgers, G. P. et al., *Circulation* 82:560 (1990); Karas, S. P. et al., *J. Amer. Col. Cardiol.* 20:467 (1992), both herein incorporated by reference) have been shown to produce arterial lesions with histopathologies which closely resemble human restenosis.

The atherosclerotic cohort (8 animals total) was initiated on a diet of 2% cholesterol, 15% fat, and 1.5% sodium cholate (Pond, W. G., In: *Swine in Cardiovascular Research*, H. C. Stanton and H. J. Morsmann, Eds. (CRC Press, Florida, 1986), Vol, 2. chap. 1) one month before catheterization. This cohort had a mean cholesterol level of 282 mg/dl during the first procedure and a mean of 266 mg/dl at sacrifice two months later.

After one month of atherosclerotic diet, the animals were sedated (IN ketamine, 20–30 mg/kg; acepromazine, 0.22 mg/kg; and atropine, 0.05 mg/kg, intubated, and anesthetized with halothane 2%. A femoral artery was isolated and a coronary guiding catheter was inserted then directed to the target coronary artery. In one major coronary, a balloon expandable flexible tantalum stent (oversized by 1.1–1.3 times the vessel diameter) was deployed under angiographic guidance. In another major coronary, balloon overstretch injury was imposed with a balloon catheter oversized by 1.1–1.3 times vessel diameter by inflating three times for 60 seconds at 8–10 atmospheres. During each instrumentation, angiography was performed to insure future identification of the target segment. The third major coronary was not instrumented and served as an uninjured atherosclerotic control. Following the procedure, the animals were maintained on atherogenic diet for two additional months until gene transfer.

The same interventional procedures described above were used to prepare for gene transfer using a strictly percutaneous approach. All three major coronary arteries in each animal underwent gene transfer using Wolinsky Infusion Catheters (USCI; Billerica, Ma.) oversized by 1.1–1.3 times the diameter of the target arterial segment. For Lipofectin™ transfection of each coronary, 50 µg of pRSVL (Keller, G. A. et al., *Proc. Natl. Acad. Sci.* (*U.S.A.*) 84:3264–3268 (1987)) was complexed with 150 µg of Lipofectin™ and diluted to a final volume of 4 ml with OptiMEM-I® (BRL). For each adenoviral infection, $4 \times 10^9$ plaque forming units of Ad5/RSV/GL2 (FIG. 1), were diluted to 4 ml with OptiMEK-I®. The infusion balloon was positioned at the previously injured target site in each coronary, 4 ml of gene transfer reagent was loaded into the inflation device, and a pressure of 8 atmospheres was applied; resulting in simultaneous balloon inflation and gene infusion over a period of 12 to 28 seconds.

Three days following gene transfer, the swine were placed under deep anesthesia and exsanguinated. The hearts were removed, placed in ice-cold PBS, and coronary arteries dissected from myocardium. The vessels were then assayed for luciferase activity using the same materials and methods described in Example 5 above.

Table 5 shows luciferase expression in atherosclerotic porcine coronary arteries including those simulating restenosis. The total amount of luciferase recovered from each atherosclerotic coronary vessel undergoing Lipofectin™- or adenoviral-mediated in vivo gene transfer is reported in picograms (pg) beneath the type of artery undergoing gene transfer: Athero, uninjured atherosclerotic, Ballooned, atherosclerotic arteries injured by oversized balloon; Stented, atherosclerotic arteries injured by intracoronary stents.

TABLE 5

ATHEROSCLEROTIC CORONARY ARTERIES

| Animal # | Athero | Restenotic Ballooned | Stented |
|---|---|---|---|
| Transfected by Lipofectin ™ (pg) | | | |
| 20 | 0.20 | 0.47 | 0.03 |
| 08 | 0.05 | 0.05 | 0.02 |
| 07 | 0.39 | 0.16 | 0.45 |
| 17 | 0.37 | 0.14 | 0.05 |
| Infected by Adenovirus (pg) | | | |
| 09 | 5.2 | 14.9 | 29.2 |
| 15 | 12.2 | 3.6 | 43.4 |
| 13 | 1.4 | 10.9 | 26.0 |
| 12 | 8.6 | 4.3 | 0.4 |

Figure 2:
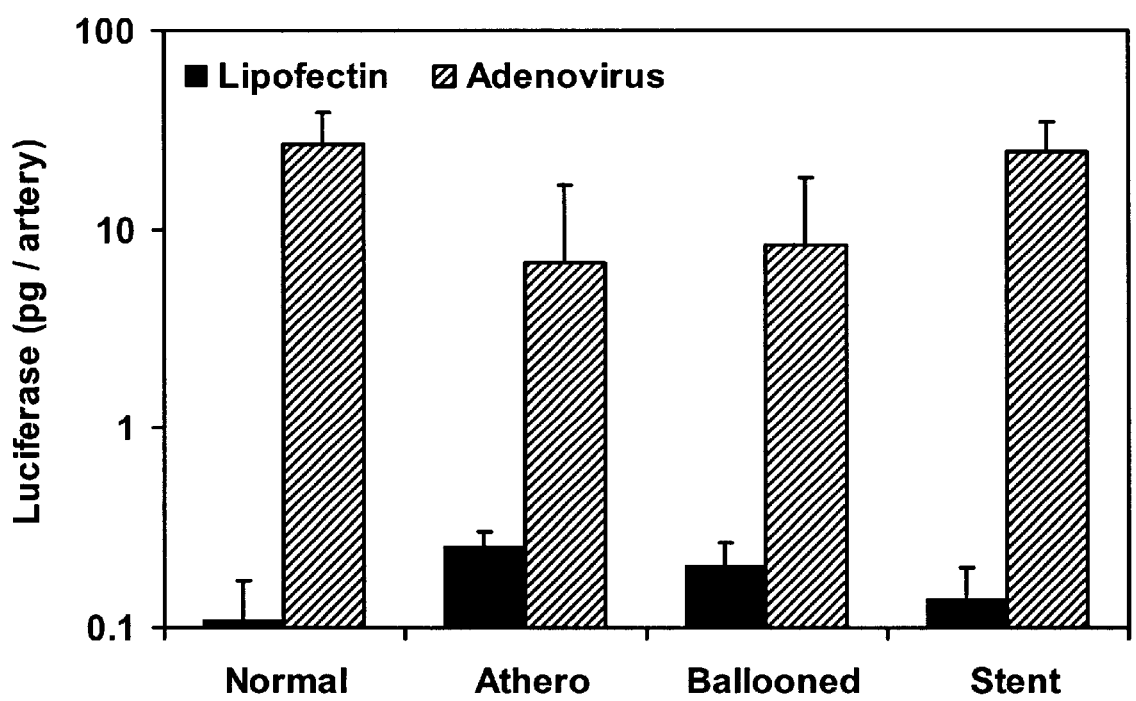
FIG. 2 shows a comparison of Lipofectin™- and adenovirus-mediated gene transfer into normal, atherosclerotic ("Athero") and restenotic porcine coronary arteries ("Ballooned" and "Stunted"). The mean picograms (pg) of active luciferase recovered per coronary artery undergoing each of the eight regimens are indicated on the y-axis. Error bars indicate standard deviation of the mean.

Table 5 demonstrates that the high efficiency provided by adenovirus-mediated gene transfer in normal coronary arteries (Table 4), can also be obtained in those with atherosclerotic and restenotic pathology. FIG. 2 summarizes the results of direct gene transfer into normal, atherosclerotic and restenotic porcine coronary arteries. In FIG. 2, the lean picograms (pg) of active luciferase recovered per coronary artery undergoing each of the eight regimens are indicated on the y-axis. Error bars indicate standard deviation of the mean.

As shown in FIG. 2, for either Lipofectin™ or adenovirus, there was no statistically significant difference in the efficiency of gene transfer between the four different types of arteries examined (Normal, Athero, Ballooned and Stented). When all arteries are divided into only two groups (those treated with Lipofectin™ and those treated with adenovirus), the luciferase levels obtained with adenovirus (mean 17.8 pg) were 100 times higher than those obtained with Lipofectin™ (mean 0.169 pg).

In order to obtain a more valid comparison of efficiency, the results were normalized to the number of luciferase genes undergoing transfer. Thus 50 µg of pRSVL DNA (10.6 pmoles of reporter gene) produced a mean 0.169 pg luciferase per coronary artery while $4 \times 10^9$ adenoviral particles (6.64 fmoles of reporter gene) produced a mean 17.8 pg luciferase per artery. Therefore, when considered on a molar basis, the adenovirus is nearly 170,000 times more efficient than Lipofectin™ at mediating direct in vivo gene transfer into porcine coronary arteries, and may thus overcome a major obstacle to gene therapy for restenosis. The differential in gene transfer efficiency is due at least in part to the molecular mechanisms by which adenovirus mediates endocytosis, endosomal disruption, and nuclear entry (Marsh, M. et al., In: *Advances in Virus Research*, K. Maramorosch et al., Eds. (Academic Press, New York, 1989), vol. 36, p. 107–151). In contrast, Lipofectin™-DNA complexes are efficient at penetrating the plasma membrane, but the majority of this DNA is lost, presumably to lysosomal degradation (Ho, S. et al., *Cytochem.* 31:404 (1983)).

The present results demonstrate that adenoviral vector mediated gene therapy provides far superior results than are obtainable with Lipofectin. The histochemical study by Nabel, E. G. et al. (*Science* 249:1285 (1990)) on the direct transfer of the lacZ gene into peripheral vessels suggested that the levels of β-galactosidase obtained with retroviral vectors were comparable to those obtained by Lipofectin™. Similarly, low levels of gene transfer using retroviral vectors were described by Flugelman, M. Y. et al. (*Circulation* 85:1110 (1992)) in rabbit aortas. Additionally, retroviral vectors may not be well suited for gene therapy against restenosis since: (i) only replicating vascular cells will express the therapeutic gene, (ii) genomic integration by retroviral vectors might interrupt vital cellular genes, or activate inappropriate genes such as cellular oncogenes, and (iii) the integrated provirus may continue to express the therapeutic gene for inappropriately long periods of time.

In contrast, replication-deficient Adenovirus 5 vectors may be particularly well suited for gene therapy since: (i) they efficiently infect vascular cells regardless of their proliferative state, (ii) the episomal location of the Ad5 genome obviates problems resulting from genomic integration, and (iii) the transient nature of adenoviral infection should result in temporary expression of the therapeutic gene. Permanent expression of therapeutic genes would be unnecessary, and perhaps deleterious, since the threat of restenosis subsides approximately 4 months after angioplasty (Serruys, P. W. et all, *Circulation* 77:361 (1988)).

In summary, experiments were thus performed with percutaneous catheters comparing the adenovirus with Lipofectin in normal arteries, atherosclerotic arteries, and in two atherosclerotic models of restenosis (employing balloon injury or stent deployment). Previous studies have established that direct invivo gene transfer into the arterial wall was possible (Nabel, E. G. et al., *Science* 249:1285 (1990)), and that Lipofectin™ and perforated balloon catheters could be used to direct such gene transfer to the coronary arteries of intact animals (Chapman, G. D. et al., *Circ. Res.* 71:27–33 (1992)). However, the limited efficiency of that technology precluded the possibility of its clinical application. In contrast to such studies, the methods of the present invention demonstrate that these problems can be surmounted in normal, atherosclerotic, and restenotic coronary arteries by using replication-deficient adenoviral vectors to accomplish direct gene transfer in vivo; and thus establishes the feasibility of using these vectors to deliver gene therapy for the prevention of restenosis following coronary angioplasty, or to provide gene therapy for other coronary or cardiovascular diseases or conditions.

Example 7

Adenovirus-Mediated Direct Gene Transfer Via Alternative Routes of Administration The examples given above detail percutaneous delivery of gene therapy to coronary arteries via a modified balloon catheter. However, a number of organs/tissues/cells can be targeted by a judicious choice of gene transfer vector and route of administration. For example, luciferase assays of porcine myocardium perfused by coronary arteries undergoing adenovirus-mediated gene transfer demonstrate that the same procedures used to obtain gene transfer into coronary arteries can also be used to obtain gene transfer into defined regions of the myocardium. Reporter gene expression following the direct injection of a gene transfer vector into the myocardium via a hypodermic needle has also been discussed in the scientific literature and confirmed in our laboratory using adenoviral vectors. These routes of administration ensure local delivery of gene transfer reagent for the purposes of confining gene therapy to a particular tissue. However, gene therapies which involve the circulatory system and/or secreted gene products do not necessarily have to be delivered to the coronary arteries or to the myocardium. For example, infusion of adenoviral vectors into the portal vein has been reported to result in high efficiency gene transfer to the liver.

Figure 3A:
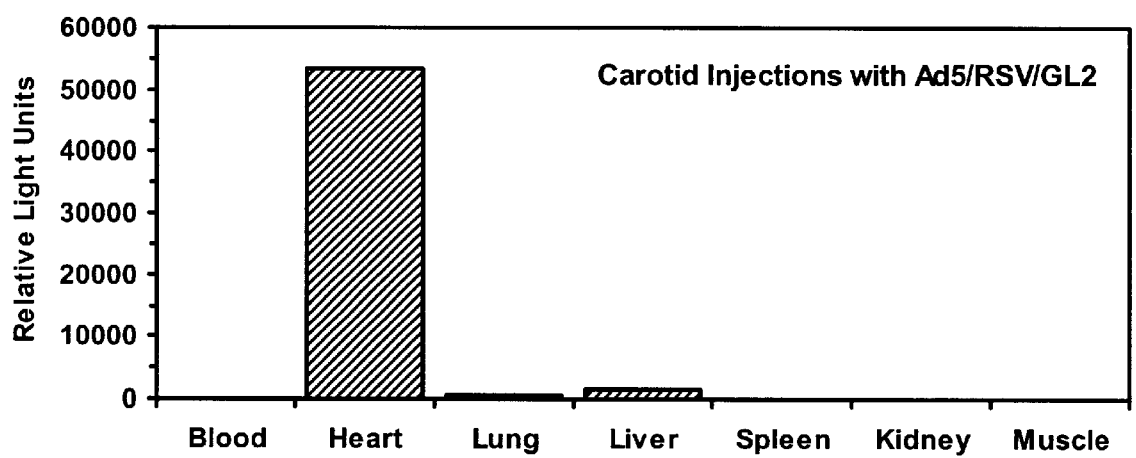
FIG. 3A shows a graph demonstrating the levels of gene expression resulting in seven neonatal rat tissues following the direct injection of Ad5/RSV/GL2 into the carotid artery.
Figure 3B:
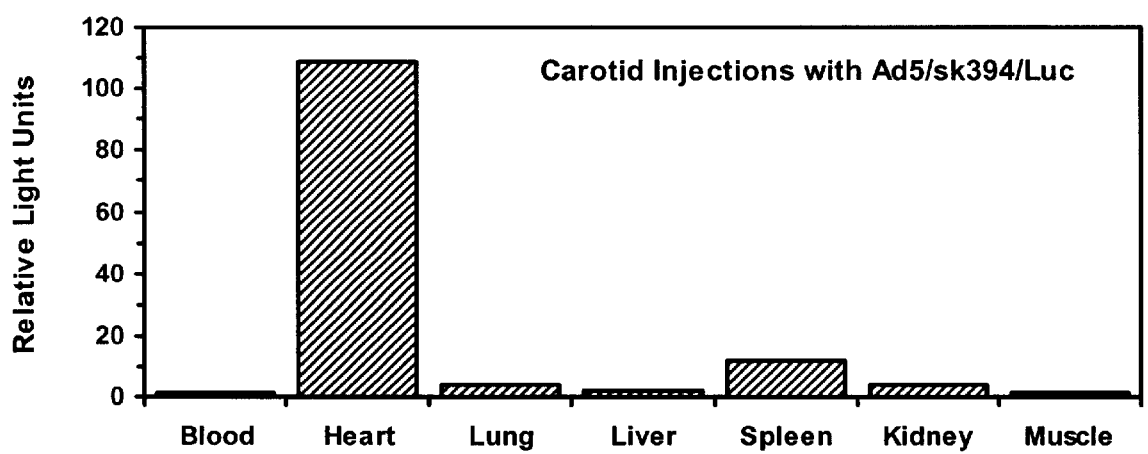
FIG. 3B shows a graph demonstrating the levels of gene expression resulting in seven neonatal rat tissues following the direct injection of Ad5/sk394/Luc into the carotid artery.
Figure 3C:
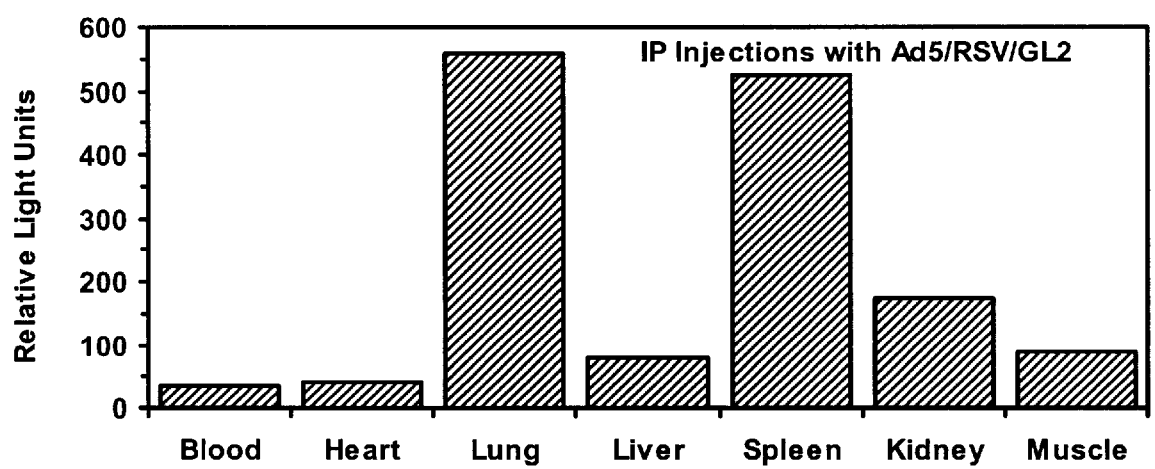
FIG. 3C shows a graph demonstrating the levels of gene expresion resulting in seven neonatal rat tissues following the direct injection of Ad5/RSV/GL2 into the peritoneal cavity.

In order to determine the pattern of gene transfer resulting from direct intraperitoneal or intra-arterial injection of recombinant adenovirus, the carotid arteries or the peritoneal cavities of 1–2 day-old rats were directly injected with adenoviral vectors via 27 gauge needles. The rats were sacrificed two days later under deep anesthesia, and seven tissue types were homogenized for luciferase determination. The relative light units of luciferase activity were normalized to the mass of tissue in the assay, and the results are presented in FIG. 3. The lower graph of FIG. 3 demonstrates that the intraperitoneal injection of Ad5/RSV/GL2 targeted vascular internal organs: chiefly the spleen and the lung, with the kidney, liver, and muscle also showing some activity. The upper graph demonstrates that the intra-arterial injection of identical amounts of the same luciferase reporter virus resulted in nearly exclusive gene targeting to the heart. The next most active organ was the liver, which had approximately $\frac{1}{30}$th the luciferase activity of the heart. Nevertheless, the luciferase activity in the liver was approximately three times higher than that obtained in the spleen or lung following IP injection. The middle graph of FIG. 3 shows the effect of employing a muscle-specific promoter to drive the luciferase reporter gene. A 394 bp fragment of the chicken skeletal a-actin promoter is positioned in front of the luciferass reporter gene in this adenoviral vector designated Ad5/sk394/Luc. The results of injecting equivalent titers of this recombinant adenovirus into the carotid artery demonstrate cardiac specificity, but the absolute levels of expression obtained in the heart are 400–500 fold lower than that obtained using the RSV long terminal repeat.

In summary, FIG. 3 demonstrates that the direct intra-arterial administration of recombinant gene transfer vectors can target the heart at high efficiency, and intraperitoneal administration can target the spleen and lung with some degree of specificity but at lower efficiency. Previous work from other laboratories demonstrates that the liver can be targeted at high efficiency using the same promoter (the RSV LTR), simply by injecting the vector into the portal vein. When combined with the Examples 1–6 demonstrating direct gene transfer into coronary arteries, it is evident that most of the tissues with relevance to the cardiovascular system can specifically be targeted via percutaneous catheterization or by simple intravascular injection. These results demonstrate that somatic gene therapy approaches to cardiovascular diseases can potentially be implemented in a; clinical setting using conventional materials and methods.

Example 8

Construction and Evaluation of Synthetic Vectors in the Treatment of Restenosis

The idea of using somatic cell gene therapy to inhibit coronary restenosis is appealing because: i) the transferred genes can express the recombinant protein within the restenotic lesion, thus reducing adverse systemic effects, ii) recombinant gene expression may be necessary for only the first few weeks after angioplasty since SMC proliferation is largely confined to this period and iii) a constitutively active gene may be adequate to suppress the restenotic process since precise regulation of gene expression may not be required.

However, the potential of gene therapy to inhibit restenosis has been severely limited by the low efficiency of gene transfer mediated by conventional methods, such as Lipofection. The inefficiency of Lipofection is attributed primarily to the lysosomal destruction of transferred DNA Ho, S. et al., *J. Histochem. Cytochem.* 31:404–420 (1983).

Coronary smooth muscle cell (SMC) culture was used as an in vitro model of the post-angioplasty vessel wall because few endothelial cells remain in the target coronary segment following the angioplasty of atherosclerotic arteries, and because the proliferative response of SMCs to high serum culture conditions in vitro resembles their hyperplastic response to vessel injury in vivo. The species-dependent variability in the susceptibility of cultured SMCs to transfection prompted a comparison of human coronary SMCs with those derived from the coronary arteries of dogs and pigs, the two large animals most commonly used to create models of cardiovascular disease.

Thus, in order to enhance transfection efficiency, cultured human, canine and porcine coronary SMCs were evaluated in two alternative methods of gene transfer. In the first, a synthetic vector was produced in which the hemagglutinin (HA) spike protein of influenza virus was added to the above-described reporter plasmid-Lipofectin™ complexes. The HA spike protein was added to test whether its membrane fusing properties (White, J. et al., *Nature* 300:658–659 (1982)) would mediate lysosomal escape and improve gene transfer efficiency. In the second method of gene transfer, a recombinant adenoviral vector was employed to directly transfer the reporter gene into SMCs. Although the natural target of the adenovirus is the respiratory epithelium (Rosenfeld, M. A. et al., *Cell* 68:143–155 (1992)), it has a wide host cell range (Lemarchand, P. at al. *Circ. Res.* 72:1132–1138 (1993); Salle, G. L. G. L. et al., *Science* 259:988–990 (1993); Quantin, B. et al., *Proc. Natl. Acad. Sci. (U.S.A.)* 89:2581–2584 (1992)) and is shown here to efficiently infect cultured SMCs. In addition, the adenovirus has been shown to possess a nuclear transport system that can further enhance gene transfer and expression.

Cell Culture

The human coronary SMCs were obtained from the recipient's explanted heart at the time of cardiac transplantation. The porcine coronary SMCs (Campbell, J. H. et al., In: *Vascular Smooth Muscle in Culture,* Campbell, J. H. et al., (eds.), Vol.1. CRC Press, 1987, pp 15–21)) were harvested from domestic swine and the canine (Feltes, T. F. et al. *Amer. J. Physiol.* 256:C169-C178 (1993)) from mongrel dogs. The coronary arteries were dissected free of overlying adventitia and minced into small pieces approximately 1 mm square. Primary cultures were established by digesting with an enzyme mixture consisting of 1 mg/ml collagenase (268 U/mg, Worthington Biochemical, Freehold, N.J.), 0.25 mg/ml elastase (Grade II, 3 U/mg, BMB, Indianapolis, Ind.), and 1 mg/ml of soybean trypsin inhibitor (Sigma, St. Louis, Mo.) in Hanks' balanced salt solution (HBSS). The cells were subsequently grown in Dulbecco's modified Eagle medium (DMEK) with 10% fetal bovine serum (FBS), 0.29 mg/ml L-glutamine, 100 U/ml Penicillin G, 100 $\mu$g/ml Streptomycin, and 25 ng/ml Amphotercin (all from GIBCO). The cultures exhibited the characteristic growth pattern (hills and valleys) of SMCs and their identity was confirmed by immunostaining with a monoclonal antibody directed exclusively against smooth muscle a-actin (Sigma). Transfections and infections were performed on SMCs between passages 3 and 5.

Transfection

The coronary SMCs were plated 24 hours prior to transfaction in 35 mm dishes at a call density of $5 \times 10^4$ cells/cm$^2$. At the time of transfection the cells were approximately 80% confluent. Transfection was performed with 1.67 $\mu$g of reporter plassid PRSVL complexed with 5 $\mu$g of Lipofectin™ reagent, DOTMA (BRL; Gaithersburg, Md.) per dish diluted in 2 ml of OptiMEM I (BRL) for 24 h. The media was subsequently changed to DMEN supplemented with 10% FBS and the cells incubated for an additional 48 h. Influenza hemagglutinin (HA) spike protein was obtained from the influenza virus vaccine, trivalent types A and B (Wyeth Lab., Marietta, Pa.). This vaccine of purified subvirion consists of 15 $\mu$g of A/Taiwan, 15 $\mu$g of B/Panama, 15 $\mu$g of A/Beijing in a volume of 0.5 ml. The vaccine stabilizer (thimerosal) was removed and the purified subvirion concentrated by multiple passages through a Centriprep-30 (Amicon Inc., Beverly, Mass.) to achieve a final concentration of 200 $\mu$g/ml as assessed by the Bio-Rad protein assay (Bio-Rad Laboratories, Richmond, Calif.). The HA spike protein in amounts of 200, 400, 800 and 1000 ng was added directly to the Lipofectin™/DNA complexes prior to dilution with OptiMEM I and transfection of SMC cultures.

Adenoviral Vector Construction, Propagation, and Infection

The plasuids pFG140 and pJM17 (Frank L. Graham, McMaster University, Ontario, Canada) are derived from the adenovirus type 5 (Ad5) dl309 genome which has a deletion in the E3 region from map units 83.5 to 85 (Graham, F. L. et al., *Meth. Molec. Biol.* 7:109–128 (1991)). A 2.2 kb plasuid (pMX2) carrying a plasuid origin of replication and an aupicillin resistance gene has been inserted at the Xba1 site in the E1 region of a circularized dl 309 genome to produce the 38.1 kb plasuid, pFG140 (Ghosh-Choudhury, G. et al., gene 50:161–171 (1986)). The replacement of the 2.2 kb pMX2 plasuid backbone in pFG140 with a larger (4.4 kb) pBR322 derivative results in pJM17, a 40.3 kb modification of the Ad5 dl309 genome which is too large to be packaged into the adenoviral capsid (Ghosh-Choudhury, G. et al., *Gene* 50:161–171 (1986); McGrory, W. J. et al., *Virol.* 163:614–617 (1988)). The plasmid pXCJL.1 contains segments from the left-end of the AdS genome, from map units 0.0–1.3 and 9.2–15.8 (Frank L. Graham, McIlaster University, Ontario, Canada). A 400 base pair (bp) segment of Rous sarcoma virus (RSV) long terminal repeat (LTR), a 1649 bp firefly luciferase cDNA, and 916 bp of SV40 sequences including the small-t intron/polyadenylation signal were inserted into pXCJL.1 between Ad5 map units 0.0–1.3 and 9.8–15.8 to generate pXCJL.1/RSV/GL2.

The recombinant replication-deficient adenovirus carrying the luciferase cDNA situated behind the RSV LTR (Ad5/RSV/GL2) was obtained through homologous recombination, in 293 cells co-transfected with the two plasmids: pJM17 and pXCJL.1/RSV/GL2. The plasmid pJM17 alone, after transfection into 293 cells, is incapable of producing a virus because the size constraints of the adenoviral capsid prevent its 40.3 kb genome from being packaged. This promotes homologous recombination between pJM17 and pXCJL.1/RSV/GL2 by selecting for the shorter recombinant which can be rescued into the adenoviral capsid. The resulting virus, Ad5/RSV/GL2 has a substitution of the luciferase expression cassette for the adenoviral E1 genes. The deletion of the E1 genes renders the adenovirus replication deficient in all cells other than the permissive 293 host which provides the E1 functions in trans. Ad5/FG140, on the other hand, was obtained by transfecting 293 cells with plasmid pFG140 alone, since its 38.1 kb can be packaged into the viral capaid. The β-galactosidase reporter virus (Ad5/HCMV/LacZ) was provided by F. L. Graham and A. Bett. This Ad5 derivative contains the human cytomegalovirus (CMV) IE promoter, *E. coli* lacz gene, and the SV40 polyadenylation signal inserted in place of the E1 region of the adenoviral genome. The Ad5/RSV/GL2, Ad5/HCNV/LacZ and Ad5/FG140 viruses were plaque-purified and propagated in 293 cells according to published protocols (Graham, F. L. et al., *Meth. Molec. Biol.* 7:109–128 (1991)) to produce viral stocks with titers of $\geq 2 \times 10^9$ pfu/nl.

Infection of porcine, canine and human coronary smooth muscle cells with the replication-deficient adenovirus was performed in 35 m dishes approaching a confluency of 80%. Serial dilutions of the recombinant adenoviruses were prepared in OptiMEN I and cells were exposed to 250 $\mu$l of the virus in OptiMEN I for 30 minutes. The titers of Ad5/RSV/GL2 used for infection were $2.5 \times 10^6$, $1 \times 10^7$, $5 \times 10^7$ and $2.5 \times 10^8$ pfu/plate. Infection with Ad5/HCMV/LacZ was carried out with viral titers of $5 \times 10^6$, $2.5 \times 10^7$ and $1 \times 10^8$ pfu/plate. The control dishes were exposed to 250 $\mu$l of Ad5/FG140 in OptiMEN I containing $2.0 \times 10^8$ pfu. After 30 minutes of exposure to the adenovirus, 1.75 ml of OptiMEN I was added to the culture plates. The medium was changed at 24 h to DMEK with 10% FBS.

In order to evaluate the affect of exposure time on infection efficiency, porcine SMCs were exposed to Ad5/RSV/GL2 for increasing periods of time. 250 $\mu$l of Ad5/

RSV/GL2 ($2.5 \times 10^8$ pfu) were added to the SMC cultures 24 h after plating at a density of $5 \times 10^4/cm^2$ in 35 mm culture dishes for exposure times ranging from 30 seconds to 30 minutes. At the end of each interval, the Ad5/RSV/GL2 was aspirated, the plates washed twice with HBSS, and DMEN with 10% FBS was added.

Luciferase Assay

Luciferase activity was assayed seventy-two hours after transfection or infection. Briefly, the SKC cultures were washed with PBS, released with 150 µl of lysis buffer (25 mM Tris-phosphate, 2 mM dithiothreitol (DTT), 2 mM EDTA, 10% glycerol and 0.1% Triton X-100) and transferred to microfuge tubes. The cell lysate was centrifuged at 12,000 g for 5 minutes, and duplicate enzymatic assays for luciferase activity were performed with 20 µl samples of supernatant using a Monolight 2010 luminometer (Analytical Luminescence Laboratory [ALL];San Diego, Calif.). A 100 µl aliquot of assay reagent (20 mM tricine, pH 7.8, 1.07 mM $(MgCo_3)_4Mg(OH)_2°5H_2O$, 2.67 mM $MgSO_4$, 0.1 mM EDTA, 33.3 mM DTT, 270 µM coenzyme A, 470 µM D-luciferin and 530 µM ATP) was added to each 20 µl sample, and the microprocessor-controlled photon counter integrated light production over a period of 30 seconds. The luminometer was calibrated using parallel reactions performed with certified firefly luciferase control standard (ALL). Background values obtained from control culture plates (equivalent to background obtained from lysis reagent) were subtracted and values were reported as the total luciferase activity recovered per 35 mm plate.

Histochemical Assay for β-galactosidase

The proportion of cells infected with various titers of Ad5/HCNV/LacZ was assessed quantitatively at 72 h by histochemical staining of SMCs for β-galactosidase activity. The SMCs were fixed in 0.5% glutaraldehyde-phosphate buffered saline, pH 7.2, for 5 min at 37° C., then stained with 5 mM $K_4Fe(CN)_6$, 5 mM $K_3Fe(CN)_6$, 2 mM $MgCl_2$, 1 mg/ml 5-bromo-4-chloro-3-indolyl-β-D galactopyranoside (X-gal; BMB) in phosphate buffered saline, pH 7.2, for 16 hr at 37° C. The proportion of cells that expressed β-galactosidase was determined by counting the number of cells stained blue in a representative sample of ≈200 SMCs per culture plate. cl Results of Lipofection With and Without HA The efficiency of gene transfer was measured by quantitating reporter gene protein per 35 mm plate by means of a luminometric assay for luciferase. Using Lipofection alone, the transfection of 1.67 µg of pRSVL produced 0.016, 2.2 and 5.2 picogram (pg) of reporter protein in human, porcine and canine SMCs, respectively. Thus the efficiency of transfection was quite low, particularly in SMCs of human origin.

In contrast, when increasing amounts of influenza HA spike protein was added to the DNA/Lipofectin™ complexes, a peak stimulation of reporter gene expression in human and porcine SMCs was obtained with 600 ng of HA per plate. The mean amounts of luciferase protein were 6.9 and 20.3 pg for human and porcine SKCs, respectively, representing approximately a 631- and 9-fold augmentation in gene product over Lipofectin™ alone. In contrast, canine SMCs were far more responsive to Lipofectin™ alone (yielding 5.2 pg/plate) and demonstrated a nearly linear dose-response relationship to HA, yielding 35.7 pg/plate at the highest dose tested (1000 ng).

Species differences in the toxicity of HA on SMCs were also observed. When ≧800 ng HA was added per plate, cell death with consequent reduction in gene product was observed in porcine and human SMCs. At 800 ng of HA per plate, toxicity was manifested as cell death in approximately 30% of these call populations. Cell death reached 70% with HA levels of 1000 ng/35 mm dish. The canine SMCS, in contrast, appeared to be unaffected by HA; even when up to 1000 ng of HA was added to a 35 mm culture plate.

Gene Transfer with Recombinant Adenovirus

The proportions of β-galactosidase positive cells in SMC cultures of human, porcine and canine origin were determined by histochemical staining with X-gal chromogen at 72 h after infection with Ad5/HCMV/LacZ. An infection rate of ≧95% was evidenced by the presence of blue chromogen in SMCs of all three species at doses of $5 \times 10^6$ pfu/35 mm plate. No evidence of β-galactosidase activity was observed in parallel experiments performed with uninfected or Ad5/FG140 ($2 \times 10^8$ pfu) infected SMC cultures after the 16 h staining period. This demonstrates that the presence of blue chromogen was due to reporter gene expression and not to endogenous β-galactosidase activity, induced either by the cell isolation, culture techniques, or adenoviral infection.

The Ad5/HCMV/LacZ dose of $1 \times 10^8$ pfu/plate was cytotoxic for human and porcine SMCs and resulted in 80% cell death. However, no toxic effects were observed in canine SMCs at similar titers of Ad5HCMV/LacZ. Cell death was not observed in SMCs of all three species infected with similar doses of Ad5/RSV/GL2.

A quantitative analysis of reporter gene product was performed by a luminometric assay for luciferase in SMCs of all species infected with Ad5/RSV/GL2. The coronary SMCs were exposed to increasing titers of Ad5/RSV/GL2 and assayed for expression of luciferase after 72 h in culture. At low doses of virus ($2.5 \times 10^6$ pfu/plate), the human and porcine SMCs had similar levels of luciferase; 17 and 12 pg, respectively. However, 7- to 10- fold higher levels of reporter gene product (126 pg) were observed in canine SMCs at the same dose. As the dose was increased to $1 \times 10^7$ pfu/plate, species differences in gene expression were less significant. At the highest titer utilized ($2.5 \times 10^8$ pfu/plate), the quantity of gene product per 35 mm culture plate was 1106, 993 and 1215 pg for human, porcine and canine coronary SMCS, respectively. These values are approximately 113,000-, 450- and 230- fold better than the best results obtained with Lipofectin alone in human, porcine and canine coronary SMCS, respectively. Thus the SMCs from all 3 species demonstrated a similar dose-response relation to adenoviral infection, suggesting that the two large animal models may well be appropriate for evaluating gene therapy protocols for inhibiting coronary restenosis.

The duration of exposure to gene transfer reagent is likely to be an important variable in intracoronary gene transfer in vivo. A transfection agent or viral vector that requires short exposure time is desirable because coronary blood flow cannot be interrupted for more than a few minutes during in vivo gene transfer. In order to evaluate this parameter, porcine SMCs were exposed for different periods of time to Ad5/RSV/GL2. An exposure duration of only 30 seconds resulted in 18 pg of luciferase protein per 35 mm plate by the luminometric assay. There was no significant difference in reporter gene product resulting from exposure times of 30 sec to 5 minutes. However, when exposure was prolonged to 15 minutes, the level of reporter gene product increased by approximately 3-fold to 43 pg. When compared with Lipofectin™-mediated gene transfer, a 15 minute exposure to 2.5×10⁸ pfu/plate of Ad5/RSV/GL2 resulted in gene expression 20-fold higher than that achieved with a 24 h of exposure to Lipofectin™/pRSVL complexes.

The data presented herein demonstrate differences in the efficiencies of gene transfer mediated by Lipofectin™ alone, Lipofectin™ plus HA, and recombinant adenovirus in SMCs of human, porcine and canine origin. The low levels of gene transfer and expression observed with Lipofectin™ alone are probably due to lysosomal degradation of the majority of endocytosed DNA. The addition of influenza hemagglutinin in the form of purified subvirion significantly improved the levels of gene transfer and expression in human, porcine and canine SMCs. This improvement is probably due to the escape of the endocytosed complex carrying the plasmid DNA from the perinuclear endosome prior to lysosomal degradation.

Unless specifically engineered to circumvent lysosomal degradation, the fate of most liposomes and their DNA content is to be endocytosed and destroyed. Several strategies have been developed to bypass this problem, including the reconstitution of the membrane proteins of influenza virus and Sendai virus into the liposomal bilayer (Mannino, R. J. et al., *Biotechniaues* 6:682–691 (1988); Kaneda, Y. et al., *Exper. Cell Res.* 173:56–69 (1987)). Technically complex methods such as detergent dialysis and modified EDTA-chelation procedures have been used to prepare these proteoliposomes (Mannino, R. J. et al., *Biotechniaues* 6:682–691 (1988)). For the HA experiments described here, the addition of influenza virus vaccine containing HA spike protein directly to the DNA/Lipofectin™ complexes provides a simple and effective means of increasing gene transfer efficiency.

Although HA augmented gene transfer when compared with Lipofectin™ alone, the best results (6.9 and 20.3 pg/plate) obtained in porcine and human SMCs were still lower than recombinant adenovirus-mediated gene transfer. Recombinant adenovirus-mediated gene transfer resulted in the synthesis of approximately 1 ng/plate of luciferase in SMC cultures of all three species. Similar levels of expression from a gene encoding an antiproliferative or anticoagulant protein would be expected to have a therapeutic effect on restenotic lesions in vivo. In addition, the ability of adenoviral vectors to mediate gene transfer during relatively short periods of exposure to SMCs is a very desirable feature considering the time constraints on the delivery of in vivo intracoronary gene therapy.

Species differences in the susceptibility of SMCs to transfection and toxicity from Lipofectin™ plus HA and recombinant adenovirus were evident. The canine SMCs were unique among the three species tested because they were readily transfected by Lipofectin™ alone and were more resistant to the cytotoxic effects of HA or recombinant adenovirus. The similarity between human and porcine SMCs in their response to these two gene transfer methods suggests that swine may be a more suitable model in which to evaluate potential transfection agents or viral vectors for the in vivo delivery of gene therapy.

In summary, in vitro studies with coronary SMCs from three species suggest that adenoviral-mediated gene transfer is highly efficient. By comparison, the technique of Lipofection (even when enhanced with HA spike protein) results in relatively low levels of gene transfer and expression. Although HA significantly enhanced the efficiency of Lipofection in coronary SMCs from all three species, the maximal enhancement was often dose-dependent. Canine cells were unique in their resistance to HA toxicity, while human and porcine cells exhibited a sensitivity to HA which resulted in cell death and decreased reporter gene expression at higher doses. Similarly, canine Slcs were resistant while human and porcine cells were sensitive to high doses of the recombinant adenovirus expressing β-galactosidase. In addition to being far more efficient than Lipofectin™-based methods, the adenovirus expressing luciferase produced similar amounts of recombinant protein in SMCs from all three species. Thus, the results of adenovirus-mediated gene therapy strategies to prevent restenosis in canine and particularly porcine models appear fully applicable to humans. The present invention demonstrates that adenovirus is an efficient vector for gene transfer into cultured SMCs and a particularly attractive candidate for the in vivo delivery of therapeutic genes into coronary arteries following angioplasty.

While the invention has been described in connection with specific ebbodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for delivering a DNA segment to a cell of a coronary artery comprising,
   administering directly to a cell of a coronary artery a replication-defective adenoviral vector comprising a DNA sequence encoding a protein effective in inhibiting restenosis operably linked to a promoter, wherein expression of said DNA sequence and production of the encoded protein results in an inhibition of intimal thickening.

2. A method according to claim 1, wherein said DNA sequence is delivered to said cells with an efficiency that is statistically greater, on a per mole basis, than that obtained when complexes of lipfectin and a plasmid comprised of said DNA sequence are infused and assayed under identical experimental conditions.

3. A method for introducing DNA segment to the nucleus of a cell of a coronary artery comprising:
   administering directly to a cell of a coronary artery a replication-defective adenoviural vector comprising a DNA sequence encoding a protein effective in inhibiting restenosis operably linked to a promoter, wherein expression os said DNA sequence and production of the encoded protein results in an inhibition of intimal thickening.

4. A method according to claim 3, wherein said DNA sequence is introduced to said nuclei with an efficiency that is statistically greater, on a per mole basis, than that obtained when complexes of lipofectin and a plasmid comprised of said DNA sequence are infused and assayed under identical experimental conditions.

5. A method for expressing a DNA segment in a cell of a coronary artery comprising, administering directly to a cell of a coronary artery a replication-defective adenoviral vector comprising a DNA sequence encoding a protein effective in inhibiting restenosis operably linked to a promoter, wherein expxression of said DNA sequence and production of the encoded protein results in an inhibition of intimal thickening.

6. A method according to claim 5, wherein said DNA sequence is delivered to said cells with an efficiency that is statistically greater, on a per mole basis, than that obtained when complexes of lipofectin and a plasmid comprised of said DNA sequence are infused and assayed under identical experimental conditions.

7. A method for inhibiting restenosis comprising, administering directly to a cell of a coronary artery a replication-defective adenoviral vector comprising a DNA sequence encoding a protein effective in inhibiting restenosis operably linked to a promoter, wherein expression of said DNA sequence and production of the encoded protein results in an inhibition of intimal thickening.

* * * * *